(12) United States Patent
Johannison et al.

(10) Patent No.: US 12,303,358 B2
(45) Date of Patent: May 20, 2025

(54) DOUBLE COATING FOR WOUND DRESSINGS

(71) Applicant: Mölnlycke Health Care AB, Gothenburg (SE)

(72) Inventors: Ulf Johannison, Landvetter (SE); Bengt Söderström, Mölnlycke (SE); AnnBritt Gergely, Mölndal (SE); Kristina Halldin, Svenshögen (SE)

(73) Assignee: Mölnlycke Health Care AB, Mölndal (SE)

( * ) Notice: Subject to any disclaimer, the term of this patent is extended or adjusted under 35 U.S.C. 154(b) by 403 days.

(21) Appl. No.: 17/783,396

(22) PCT Filed: Dec. 16, 2020

(86) PCT No.: PCT/EP2020/086387
§ 371 (c)(1),
(2) Date: Jun. 8, 2022

(87) PCT Pub. No.: WO2021/122720
PCT Pub. Date: Jun. 24, 2021

(65) Prior Publication Data
US 2023/0009183 A1    Jan. 12, 2023

(30) Foreign Application Priority Data
Dec. 19, 2019   (EP) .................................... 19218022

(51) Int. Cl.
*A61F 13/00* (2024.01)
*A61F 13/02* (2006.01)
(Continued)

(52) U.S. Cl.
CPC ........ *A61F 13/022* (2013.01); *A61F 13/0209* (2013.01); *A61F 13/0289* (2013.01);
(Continued)

(58) Field of Classification Search
CPC .. A61F 13/022; A61F 13/025; A61F 13/0209; A61F 13/0289; A61F 13/0276;
(Continued)

(56) References Cited

U.S. PATENT DOCUMENTS

2019/0351094 A1   11/2019   Maher et al.

FOREIGN PATENT DOCUMENTS

| EP | 0538917 A1 | 4/1993 |
| EP | 0633758 B1 | 10/1996 |

(Continued)

OTHER PUBLICATIONS

International Preliminary Report on Patentability was mailed on May 17, 2022 by the International Searching Authority for International Application No. PCT/EP2020/086387 filed on Dec. 16, 2020 and published as WO2021122720A1 (Applicant—Molnlycke Health Care AB) (8 pages).
(Continued)

*Primary Examiner* — Victoria Hicks Fisher
(74) *Attorney, Agent, or Firm* — Ballard Spahr LLP

(57) ABSTRACT

A medical dressing is described that includes: a porous layer having a first side and a second side; a first coating extending along at least a portion of the surface area of said first side of said porous layer; a second coating extending along said first side of said porous layer, said second coating comprising a pattern of through openings; wherein said first coating extends along at least those portions of the surface area of said first side of said porous layer that coincide with the through openings of said second coating and wherein said first surface of said second coating extends in a plane (B) that is farther away, in the vertical direction, from the first side of said porous layer, than the corresponding plane (A) defined by the first surface of said first coating.

13 Claims, 8 Drawing Sheets

(51) Int. Cl.
*A61F 13/0203*    (2024.01)
*A61F 13/0206*    (2024.01)

(52) U.S. Cl.
CPC ............... *A61F 2013/00702* (2013.01); *A61F 2013/0074* (2013.01); *A61F 2013/00863* (2013.01)

(58) Field of Classification Search
CPC ............ A61F 13/02; A61F 2013/00863; A61F 2013/0074; A61F 13/0203; A61F 13/0279; A61F 13/0206; A61F 13/0246; A61F 2013/00761; A61F 2013/00778; A61F 13/00; A61F 13/15; A61F 2013/15569; A61F 13/536; A61F 13/533; A61F 13/539

See application file for complete search history.

(56)    References Cited

FOREIGN PATENT DOCUMENTS

| EP | 0855921 B1 | 1/2002 |
| WO | WO 2015/130471 A1 | 9/2015 |
| WO | WO 2016/109418 A1 | 7/2016 |

OTHER PUBLICATIONS

International Search Report and Written Opinion were mailed on Apr. 9, 2021 by the International Searching Authority for International Application No. PCT/EP2020/086387 filed on Dec. 16, 2020 and published as WO 2021/122720A1 (Applicant—Molnlycke Health Care AB) (11 pages).

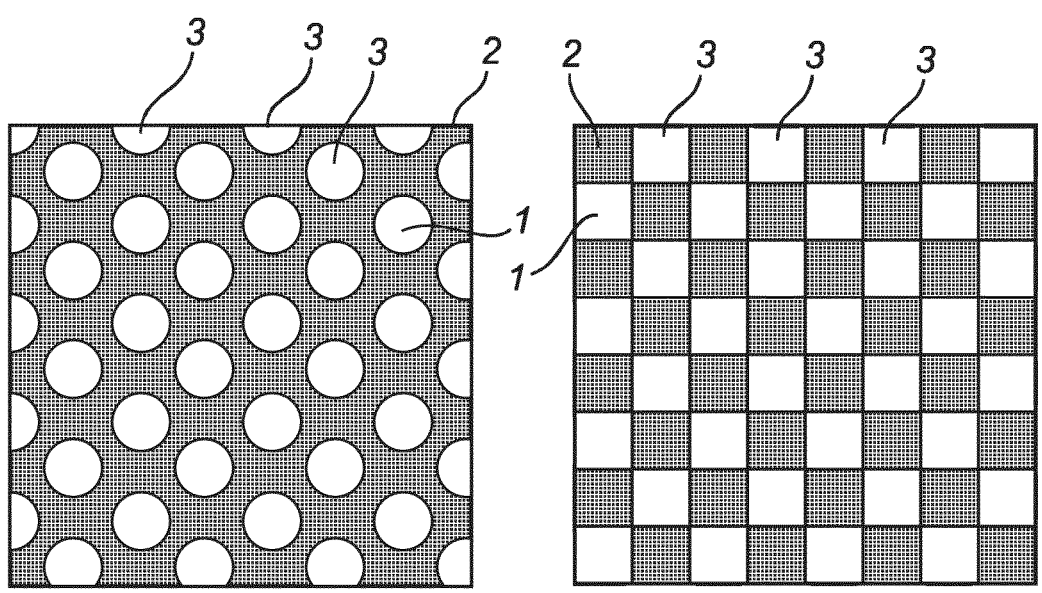
*Fig. 3A*    *Fig. 3B*

DOUBLE COATING FOR WOUND DRESSINGS

CROSS-REFERENCE TO RELATED APPLICATIONS

This application is a U.S. National Phase Application of International Application No. PCT/EP2020/086387, filed Dec. 16, 2020, which claims priority to European Application No. 19218022.2, filed Dec. 19, 2019, each of which are hereby incorporated by reference in their entirety.

FIELD OF THE INVENTION

The present invention relates to a wound dressing having improved capabilities to retain wound exudate in a porous layer, and to a method for producing a wound dressing.

BACKGROUND OF THE INVENTION

Wound dressings are used to heal, protect and prevent wounds. The capability of wound dressings to absorb and retain exudate from the wound is of paramount importance for the healing process. The fluid handling capacity of a dressing also affects the frequency of dressing changes, which should be minimized to promote wound healing.

Hydrophilic materials are used advantageously in wound dressings to absorb and retain wound fluids, in particular hydrophilic foams such as hydrophilic open-cell polyurethane foams. Absorbent fiber arrays and networks (e.g. non-wovens, gelling fibers, hydroentangled fibers etc.) may also advantageously be used in fluid management/fluid handling.

To ensure that a wound dressing stays on and seals around the wound, the dressing typically includes an adhesive layer that is in physical contact with the wound and/or the surrounding skin (peri-wound area).

Silicone based adhesives (in particular "soft" silicone gels) are known in the art, in principle, as being particularly useful as the skin-contact surface in wound dressings. In particular, silicone based adhesives adhere well to dermal surfaces but do not (or not significantly) stick to moist wound surfaces and therefore cause less or no pain and/or trauma to the skin upon removal of the dressing, in particular when compared to other commonly used adhesives, for example acrylic adhesives.

The silicone adhesive layer may be provided as a coating directly on an absorbing layer of the dressing. Such silicone coatings typically have a pattern or array of through holes ("perforations") in order to facilitate fluid transport through the wound contact layer, in particular to facilitate transport of wound exudate from the wound to those parts of a wound dressing that absorb, retain and ultimately transport away wound exudate, for example a porous or absorbent layer.

As an example, EP 0 855 921 discloses a dressing comprising an absorbent foam layer which is coated, on one side, in particular on the wound facing side of the foam layer, with a silicone gel adhesive. EP 0 855 921 discloses in one embodiment that the silicone gel layer extends slightly into open pores of the absorbent foam material (without, however, "closing" all pores). In this embodiment, some foam pores are covered by a continuous layer of said silicone gel, and although this is advantageous to prevent spontaneous reflux of absorbed fluid from the absorbent foam layer back to the skin or the wound, wound fluid transportation overall is then limited to the remaining "open" pores. This may be seen as affecting the overall absorption capacity of the dressing.

One option to increase the fluid handling capacity of such a foam layer is to cut holes in the absorbent foam material thereby creating channels in the foam material through which wound fluid can be absorbed. Providing such channels or openings, however, may be associated with increasing the risk of undesirable spontaneous reflux of absorbed fluid to the skin or the wound as the area of uncoated foam surface is increased.

EP 0 633 758 discloses a wound dressing comprising a layer of silicone gel, a layer of carrier material and an absorbent body, wherein the carrier material and the silicone gel layer have mutually coinciding penetrating perforations at least within the region of the absorbent body. Thus, wound exudate can be transported through the perforations and can be absorbed by the absorbent body. However, in the area of these perforations, the absorbent body is directly exposed towards the wound, which may be associated with increasing the risk of reflux of absorbed fluid to the skin or the wound.

Hence, there is a need in the art to provide a wound dressing with an adhesive layer that avoids or minimizes all or some of the disadvantages discussed above. In particular, a wound dressing for wound contact is to provided that improves fluid management and, further particularly, minimizes or avoids reflux of wound exudate from an absorbent layer (e.g. an open cell foam or a fiber array with openings/pores) back to the skin or the wound of a patient.

SUMMARY OF THE INVENTION

In view of the above-mentioned and other drawbacks of the prior art, one object of the present invention is to provide a dressing for the treatment of wounds, and a method to produce the same, which wound dressing does not suffer from the disadvantages outlined above, or at least minimizes some or all of these disadvantages, in particular which wound dressing minimizes reflux of wound exudate from an absorbent layer (e.g. an open cell foam body) that is part of said wound dressing back to the skin or the wound of a patient.

According to a first aspect of the invention, these and other objects are achieved through a medical dressing (20), said medical dressing (20) comprising:

a porous layer (10) having a first side (11) and a second side (12), wherein said first side and said second side are opposite to each other and extend in the horizontal direction of said porous layer;

a first coating (1) extending along at least a portion of the surface area of said first side (11) of said porous layer (10), optionally along essentially the entire surface area of said first side (11), wherein said first coating (1) has a first surface facing away from said first side of said porous layer;

a second coating (2) extending along said first side (11) of said porous layer (10), said second coating (2) comprising a pattern of through openings (3), wherein said second coating (2) has a first surface facing away from said first side (11) of said porous layer (10);

wherein said first coating (1) extends along at least those portions of the surface area of said first side (11) of said porous layer (10) that coincide with the through openings (3) of said second coating (2);

and wherein said first surface of said second coating (2) extends in a plane (B) that is farther away, in the vertical direction, from the first side (11) of said porous layer (10), than the corresponding plane (A) defined by the first surface of said first coating (1).

In accordance with the present invention, a "medical" dressing is a dressing that is used to treat or prevent any type of wound or injury or condition on the skin of a human or an animal, in particular such wounds or conditions that involve or require the removal of fluid, in particular the removal of wound exudate. In embodiments, medical dressings are wound dressings. In accordance with the present invention, the term "wound site" or "wound" is to be understood as any open or closed wound, for example, including inter alia (but not limited to) chronic wounds, acute wounds, and post-operative wounds such as e.g. closed incisions and scars.

A "layer" in accordance with the present invention should be understood to have a continuous extension in a horizontal direction ("x"- and "y"-direction) and in a vertical direction ("z"-direction; commonly referred to as "thickness") perpendicular to said horizontal direction. In embodiments, said porous layer extends at least five times, preferably at least ten times, more in the horizontal direction than in the vertical direction.

A "porous" layer in accordance with the present invention should be understood to be a layer that has a porous texture, i.e. comprises pores, channels or openings, the volume of which in not zero and which volume can be determined by standard methods for determining the internal volume of porous bodies. One example of such a porous layer is open cell foam, i.e. a foam, for example a polyurethane foam, that comprises a plurality of mutually connected pores so that a fluid can penetrate from one side of the foam to the other. Open cell foams in the meaning of the present invention also may comprise closed pores/cells, i.e. not all pores of a given foam segment need to be connected (with each other).

Another example of a porous layer is an array of fibers, e.g. an array of superabsorbent fibers, or of gelling fibers (e.g. Exufiber®), or a network of fibers, e.g. a non-woven (e.g. Fibrella®), including hydroentangled fibers, in particular as present in non-woven network, or any combination of any of the above, either with each other or with other components, such as superabsorbent particles.

The term "coating" as used in accordance with the present invention should be understood as providing a layer that at least partially covers a substrate and wherein said layer is a material distinct from the substrate and at least partially in physical contact with said substrate.

A "coating" in the meaning of the present invention does not need be "continuous" in the sense that the coating covers or "overcoats" the entirety of the substrate that the coating extends along. Rather, as is perhaps best illustrated in the SEM pictures of FIGS. 1B and 1C (and also schematically hinted at in the drawings of FIGS. 1A, 2 and 2A) both coatings (1) and (2) may have holes or may be broken up. In particular coating (1), which has the primary purpose of rendering the surface of the porous layer (10) (more) hydrophobic may be quite broken up and may have, in fact, more holes and openings than being coherent coating surface, but is still a "coating" in the meaning of the present invention. In particular, the coating (1) may be comprised of a plurality of portions (i.e. "dots", "islands" or "spots") which are not connected with each other (see SEM photograph of FIG. 1B, which shows a porous foam "skeleton" having unconnected portions of silicone gel). As can be seen in the SEM of FIG. 1C, the coating (2) typically has less holes and is more coherent as a coating than coating (1). A fully coherent/continuous coating (2) is, of course, also a "coating" in the meaning of the present invention.

In embodiments of the invention, the coating (1) extends over essentially the entire first side (11) of the porous layer (10). This embodiment is particularly advantageous in case the porous layer (10) and/or the coating (2) is/are such that a significant number of such "natural" holes are formed (for example because the first side of the porous layer has a surface that has a large number of larger pores which give rise to "natural" holes if the coating (2) is applied directly on such surface), since also these "natural" holes (in particular if they are large) may give rise to reflux and thus benefit from being made (more) hydrophobic by the first coating (1). Apparently, the occurrence of these "natural" holes is essentially unpredictable, which is why it is advantageous to coat essentially the entire first side in case a larger number of such "natural" holes occurs in the second coating (2).

The term "surface" of a substrate or layer as used in accordance with the present invention should be understood as that part of the substrate or layer that defines the outer border of said substrate or layer. Depending on the resolution with which the surface is viewed, the surface may be, or may appear, even, smooth or rough ("fractal"). The surface area may comprise openings or pores that themselves also have "surface" defining the boundary between the substrate or layer vis-à-vis the "outside" of said substrate or layer, for example the boundary vis-à-vis air.

In accordance with the present invention, if a coating extends "essentially" over the entire surface area of a layer, this is understood to mean that at least 70% of the surface as visible to the eye (excluding any internal surfaces) are covered by the coating, preferably at least 90%. As mentioned above, the fact that a given coating extends along essentially all of a substrate, or a large part thereof, does not exclude that the coating itself may be broken up or have holes, as discussed above and as shown in the SEM photographs of FIGS. 1B and 1C.

The term "pattern" of through openings ("perforations") as used in accordance with the present invention should be understood as any regular, in particular geometrically arranged patterns, but any irregular array of through openings is also a "pattern" in the meaning of the present invention.

Said pattern of through openings, regular or irregular, may also be achieved by way of coating silicone gel in the form of "lands" or "strings" directly onto the porous layer and leaving through openings between those land or strings.

The term "through openings" in a coating as used in accordance with the present invention should be understood as any "hole" or perforation in a coating or layer. No limitations exist, in principle how to create these through openings in a coating.

As discussed above, any coating in accordance with the present invention may have "natural" holes that occur unpredictably during coating. Above and beyond the possible existence of such "natural" holes, the pattern of through openings (3), in particular through openings in a regular pattern, are purposefully formed. Such "purposeful" formation of a pattern of through openings may be achieved, for example, by coating a porous layer having an array depressions or openings (see FIG. 1 and FIG. 2), wherein said array of depressions or openings leads to the formation of the pattern of through openings during the step of coating, in particular the step of transfer coating. Alternative approaches to achieve a coating (2) with a pattern of through openings includes, among others, subjecting the coating to a perforation step, for example ultrasonic perforation (before, during or after curing), or by pattern coating methods (e.g. to produce a "chess" coating pattern using a moving nozzle).

In embodiments, these through openings have an essentially circular circumference. In other embodiments, the circumference may be oblong or rectangular/square (see, e.g. FIG. 3B).

The term "plane" as used in accordance with the present invention should be understood as a horizontal plane that extends along the outer surface of a coating. If the coating is regular and has no noticeable variations in thickness, this plane essentially coincides with the outer [the farthest away from the first side (11) of the porous layer] surface of the coating. If a coating is irregular in thickness, for example has indentations, distortions or is bulged, the plane will be defined by the outermost [the farthest away from the first side (11) of the porous layer] distortions.

The terms "horizontal" and "vertical" as used in accordance with the present invention should be understood in their conventional meaning, as illustrated in FIG. 1. Any coating in accordance with the present invention will extend significantly more in the horizontal direction than in the vertical direction.

In embodiments of the present invention, the dressing comprises a second coating (2), which has a pattern of through openings (3), which coating is intended to be in (direct) contact with an area of application in use (in particular a wound site), wherein the primary purpose of said second coating (2) is to ensure that the medical dressing is held in place by providing an adhesive coating, while generally allowing, at the same time, for a fluid (in particular wound exudate) to be transported to the porous layer (10) through said pattern of through openings (3).

While said pattern of through openings (3) is advantageous for improving fluid transportation through the coating, said pattern of openings may increase the risk of undesirable reflux of absorbed liquid, i.e. liquid s (e.g. exudate) may leak back out (i.e. back to the wound site) from the medical dressing, in particular from the porous layer, through said through openings.

The present invention is partly based on the realization that such reflux (or back-leakage) of absorbed fluid from a medical dressing, in particular reflux of wound exudate from a wound dressing may be minimized by a "double" coating system, wherein a first coating (1) is provided on at least those portions of the surface area of a porous substrate which are not coated by a second coating (2), i.e. at least in the area of said pattern of through openings, which portions of the surface area of the porous substrate or layer would otherwise be (directly) exposed to the wound site. While it is sufficient for achieving this advantageous outcome that said first coating is only or primarily provided on those parts of the surface area of the porous substrate that coincide with the through holes of the second coating (i.e. that are exposed to the wound), said first coating may also cover other parts of the surface area of the porous substrate or may even cover all or essentially all of said surface area, which, in fact, is advantageous from a processing point of view.

In embodiments of the present invention, the first coating (1) is or comprises a hydrophobic material. Thereby, the presence of absorbed liquid specifically in the vicinity of the surface area of the porous layer on which the first coating is present is minimized. Without wishing to be bound by theory, it is believed that making the surface area of the porous layer (10) (more) hydrophobic by way of coating the first side of said porous layer with a hydrophobic coating, for example with a silicone gel, the hydrophobic coating acts as a barrier or "one-way valve" against reflux of the wound exudate from the porous layer back to the wound, i.e. allows fluid to pass from the wound to the porous layer but avoids or minimizes flow from the porous layer back into the wound (or onto the skin).

In accordance with the present invention, the term "hydrophobic" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to the association of non-polar groups or molecules in an aqueous environment, which arises from the tendency of water to exclude non-polar molecules.

In embodiments of the present invention, the first coating (1) and the second coating (2) are different in at least one of the following properties: initial weight of coating as applied, material composition, tackiness or hydrophobicity, or any combination thereof, preferably wherein said first coating (1) is applied in at a weight that is smaller than the of the second coating (2).

In embodiments of the present invention, the second coating (2) has a primary function of being tacky or adhesive, i.e. a primary function is to provide adhesion to the skin of a patient, while the first coating (2) has a primary function of rendering the first side of the porous layer (10) hydrophobic.

The term "tackiness" as used in accordance with the present invention should be understood as a surface tack of at least 1 N as measured by the FINAT Test Method 9 Loop tack measurement on a coating having a coating weight of 5 gsm.

In embodiments of the present invention, the pattern of through openings (3) in the second coating (2) is a regular geometric pattern or array, preferably represents a circular, rectangular or trapezoidal array of through openings (3).

In embodiments of the present invention, the average diameter of the through openings (3) is from 50 μm to 5 mm, optionally 100 μm to 3 mm, further optionally 500 μm to 2 mm.

In embodiments of the present invention, the average spacing of the through openings (3) as measured from their respective geometric centers, within the plane of the coating is from 1 mm to 10 mm, optionally from 2 mm to 5 mm.

In embodiments of the present invention, the through openings (3) make up from 1% to 20% of the entire surface area of the second coating (2), optionally from 2% to 10%.

In embodiments of the present invention, the second coating (2) is an adhesive coating, optionally a silicone based adhesive coating.

In embodiments of the present invention, the first coating (1) is a silicone-based coating.

In embodiments of the present invention said first coating (1) has a coating weight of from 5 $g/m^2$ to 70 $g/m^2$ or from 10 $g/m^2$ to 50 $g/m^2$ or from 10 $g/m^2$ to 30 $g/m^2$.

In embodiments of the present invention said second coating (2) has a coating weight of from 50 $g/m^2$ to 500 $g/m^2$ or from 100 $g/m^2$ to 300 $g/m^2$.

Since the first coating (1) does not have the primary function, or, in fact, any functionality to provide adhesive properties, its amount (weight as initially applied) can be significantly lower than the coating weight of the second coating (2).

In embodiments of the present invention, said porous layer (10) comprises an absorbent material, optionally wherein the porous layer (10) is or comprises a hydrophilic open-cell foam.

In accordance with the present invention, the term "hydrophilic" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to the capacity of a molecular entity or of a substituent to interact with polar solvents, in particular with water, or with other polar groups.

In regard to foam as the porous layer, the term "hydrophilic" generally refers to the water-permeability of the foam or the water-attracting property of the foam. In the context of materials with pores (such as, for example, open-cell foams) or materials with through-holes, such a material is generally considered "hydrophilic" if the material takes up water.

In embodiments of the present invention, said foam has a hardness of 1.0 to 6.0 kPA measured according to ISO 3386-1 at 40% compression.

In embodiments of the present invention, the density of the foam is from 20 to 40 kg/m$^3$, optionally from 25 to 35 kg/m$^3$ measured according to ISO 845.

In embodiments of the present invention, the foam at 25% elongation has a wet elasticity higher than 6 kPa and a dry elasticity higher than 13 kPa measured according to a method described in WO 2009/126102.

In embodiments of the present invention, the cell diameter in said foam is between 500 to 1,800 μm, and preferably 1,100 to 1,500 μm measured according to Visiocell SS-T.013.4E.

In alternative embodiments of the porous layer (10) of the present invention, which are perhaps best illustrated in FIGS. 4A and 4B, the porous layer (10) is or comprises an array of fibers, in particular an array of superabsorbent fibers, or of gelling fibers (e.g. Exufiber®).

In accordance with the present invention, an array of fibers is any arrangement of fibers that has a larger extension in a (x-y) plane than in the direction perpendicular thereto (z-direction). Preferably the array of fibers has an area weight ("grammage") of 20-500 g/m$^2$, preferably 50-350 g/m$^2$.

In further alternative embodiments of the porous layer of present invention, the porous layer (10) is or comprises a network of fibers, in particular a non-woven (e.g. Fibrella®), including hydro-entangled fibers, in particular hydro-entangled fibers in a non-woven network.

For example, in embodiments of the invention, the porous layer (10) is or comprises an air-laid material comprising synthetic stable fibers and/or bi-component stable fibers and/or natural stable fibers and/or superabsorbent fibers and/or superabsorbent particles.

In accordance with the present invention, and also in accordance with the universally accepted understanding of the skilled person, a "non-woven" is defined as sheet or web structures bonded together by entangling fiber or filaments mechanically, thermally, or chemically, but not (as is conventionally done for fabrics) by weaving or knitting. Non-wovens are defined by ISO standard 9092 and CEN EN 29092. Non-woven substrates or webs are typically flat, porous sheets that are made directly from separate fibers or from molten plastic or plastic films.

In embodiments of the present invention, the thickness of said porous layer (10) in any of the above embodiments is from 0.5 mm to 30 mm, optionally from 1 to 15 mm, optionally thereto from 1 to 10 mm.

In embodiments of the present invention, said first coating (1) is provided in direct physical contact with the surface area of said first side (11) of the porous layer (10), and wherein said second coating (2) is provided in direct physical contact with said first coating (1).

In other embodiments, at least one further layer, for example a perforation layer (see FIGS. 4A and 4B) is/are arranged between the first and the second coating, i.e. the second coating is applied indirectly over said first coating.

In embodiments of the present invention, the first surface of the first coating is substantially "co-planar" with the first surface of the porous layer.

In embodiments of the present invention, the first coating (1) has penetrated into at least 10% of the thickness of the porous layer (10), optionally the first coating (1) has penetrated into at least 40% of the thickness of the porous layer (10), optionally thereto the first coating (1) has penetrated into essentially the entire thickness of the porous layer (10).

The "penetration depth" of the first coating (1) into the porous layer (10) depends, among others, on whether only one porous layer is present in the overall dressing, which one porous layer then has the functionality to achieve the absorption capacity of the entire dressing. In such a case, it may be preferred that the first coating (1) (only) penetrates into 50% of the thickness of the porous layer (1), while penetrating at least 10%.

In other scenarios, in which a comparatively thin first porous layer is provided and then a second porous layer, it may be advantageous if the first coating penetrates through the entire thickness of the first porous layer.

Without wishing to be bound by theory, it is the understanding of the inventors that the degree of penetration of the first coating (1) into the porous layer (10) allows to optimize the degree of hydrophobicity of the surface [first side (11)] of the porous layer (10) that is exposed to the wound through the through openings (3) of the second coating (2). For example, if the through openings are comparatively large in diameter or comparatively closely spaced, it may be advantageous to provide a higher degree of hydrophobicity on the surface of the porous layer by way of increasing the penetration depth of the first coating into said porous layer. It may also be advantageous in such a scenario to provide one relatively thin first porous layer that is fully penetrated by the first coating and then providing a second porous layer that is not made hydrophobic.

In embodiments of the present invention, and as perhaps best illustrated in FIG. 1 and FIG. 1B, said porous layer (10) comprises a pattern of depressions (25, 25'), wherein said pattern of depressions (25) is present on both said first side (11) and said second side (12) of said porous layer (10), wherein said pattern of depressions (25) on the first side is coaxial to the pattern of depressions (25') on the second side and wherein the two patterns of depression (25, 25') are separated from each other by a common portion (10') of the porous layer, which common portion (10') is compressed to a higher extent than the remaining parts of said porous layer (10).

In embodiments of the present invention, said pattern of depressions (25, 25') is the result of ultrasonic treatment.

In alternative embodiments of the present invention, and as perhaps best illustrated by FIG. 2, said porous layer comprises a pattern of openings (15), wherein said pattern of openings (15) is provided in said first side (11) of said porous layer (10), preferably wherein said openings (15) do not fully penetrate said porous layer (10).

In embodiments of the present invention, said pattern of openings (15) is the result of laser treatment or treatment by heated pins.

In embodiments of the present invention, said pattern of openings (15) or depressions (25) in the porous layer (10)

substantially coincides with said pattern of through openings (3) in said second coating (2).

In embodiments of the present invention, the first coating (1) is provided on at least that portion of the surface area of said porous layer (10) that has said openings (15) or depressions (25), or in other words, the portion of the surface area of the porous layer on which said first coating (1) is provided is at least the portion of the surface area with said openings (15) or depressions (25) in the porous layer.

In embodiments of the present invention, as illustrated in FIG. 4A and 4B, the medical dressing (20) further comprises a perforated layer (21) comprising a pattern of through openings, said perforated layer (21) having a first side and a second side wherein the first side of the perforated layer (21) is arranged to face away from the first side (11) of the porous layer (10), wherein the second coating (2) is provided on the first side of the perforated layer (21), and wherein the pattern of through openings (3) in the second coating (2) substantially coincides with the pattern of through openings (3') in the perforated layer (21).

In embodiments of the present invention (as also illustrated in FIGS. 4A and 4B), the medical dressing further comprises a backing layer (22) extending over the second side (12) of the porous layer (10).

According to a second aspect of the invention, the above-mentioned and other objects are achieved by means of a method for manufacturing a medical dressing, said method comprising the steps of:
providing a porous layer (10) having pores or openings;
applying a first coating (1) onto a first side (11) of said porous layer,
compressing said porous layer (10) such that said applied first coating (1) at least partly penetrates into the pores or openings of the porous layer,
directly or indirectly applying a second coating (2) over said first side (11) of said porous layer (10),
introducing a pattern of through openings (3) into said second coating (2), either prior to said step of applying a second coating (2), or during said step of applying a second coating (2), or after said step of applying a second coating (2);
wherein, after conclusion of these steps, said first coating (1) extends along at least those portions of the surface area of said first side (11) of said porous layer (10) that coincide with the through openings (3) as introduced into said second coating (2).

In embodiments of the present invention said first coating (1) has a coating weight of from 5 g/m² to 70 g/m² or from 10 g/m² to 50 g/m² or from 10 g/m² to 30 g/m².

In embodiments of the present invention, the weight of said second coating (2) as applied is at least 30% more, optionally at least 50% more than the weight of the first coating (1) as applied.

In accordance with the present invention, the silicone composition as applied in the first and in the second coating may be the same or may be different (in terms of composition and chemistry). However, as outlined above the amount (weight) is generally different and, in particular, lower for the first coating than the second coating as applied.

In embodiments of the present invention, said first coating (1) is or comprises a first silicone composition, which is applied over said first side (11) of said porous layer (10) in a substantially uncured state, and wherein said method further comprises a step of curing said first silicone composition after said step of compressing said porous layer.

In embodiments of the present invention, said silicone gel of said first coating (1) is applied as silicone gel in uncured state over one side of the porous layer (10), wherein said layer with the applied silicone gel is fed between two webs of process paper through a pair of press rolls, between which press rolls the foam with the applied silicone gel is compressed, optionally wherein said two webs of process paper (that may comprise excess silicone gel if the layer is fully impregnated) are removed and the as-coated porous layer (10) is heated for curing of the silicone gel.

According to an embodiment of the present invention, the method is further characterized in that the curing of the silicone gel is performed in a hot blast furnace at a temperature of about 100° C. for about 1 to 5 minutes, preferably for about 3 minutes.

According to an embodiment of the present invention, the process is characterized in that the pressure between the press rolls is from 3 to 10 bar, optionally from 3 to 7 bar, optionally from 2 to 5 bar.

Said pressure is advantageously adjusted to achieve the desired degree of penetration into the porous layer (10) with the silicone gel coating (1). Control of the degree of penetration into the layer may be performed by microscopy or, in case full impregnation is desired, by inspecting the two webs of process paper, which both paper webs are coated with silicone gel when the foam web is fully impregnated.

In embodiments of the present invention said second coating is or comprises a silicone composition which is applied over said first side of said porous layer as coated with coating (1) in a substantially uncured state, and wherein said method further comprises a step of curing said second silicone coating (2) after it has been applied over said first coating.

In embodiments of the present invention, said step of curing said first silicone coating (1) and said step of curing said second silicone coating (2) are performed at the same time.

In embodiments of the present invention, said first coating is applied by a compression step (cf. FIG. 5), i.e. a step in which sufficient pressure is applied to said first coating (1) so that at least a part of said first coating penetrates into pores or openings of the porous layer (10) while the porous layer is being compressed, and said second coating is applied by method comprising a transfer coating step (cf. FIG. 6), wherein the pattern of through openings in the second coating is introduced during or after said transfer coating step.

Other coating techniques, e.g. dipping techniques are also included in the scope of the claimed method.

In other embodiments, the second coating (2) is not applied directly onto the first coating but rather onto a separate layer that then may be perforated [see, e.g. perforation layer (21) in FIG. 4B], which is then bonded together with a porous layer (10) that is already coated with coating (1) (see FIG. 4A through 4D).

In embodiments of the present invention, when coating the second coating (2) over the porous layer (10) using a step transfer coating, the silicone gel is pressed into the foam surface and the applied pressure is configured such that a desirable amount of silicone gel is left on the foam surface to provide the desired adhesive properties. Hence the pressure applied upon transfer coating may be used advantageously to modulate the adhesive properties of the overall dressing.

Without wishing to be bound by theory, it is believed that the application of pressure in the compression step, as outlined above, ensures or aids sufficient penetration of first coating (1) into the porous layer (10) and, subsequently, when the compressed foam expands (as the applied pressure is released), breaks all or most of any "continuous" or "blocking" films of the coating that may have formed inside the pores such that, at the end of the compression and expansion of the porous layer, the first coating is present on the cell walls of the pores but does not form a coherent film leading to "blockage" in or between open-cells (see FIG. 1C for an SEM photograph of essentially open pores that are not covered/blocked by coating (1) but are rendered hydrophobic by virtue of a thin silicone gel coating on the walls constituting the pores).

By contrast, applying the second coating (2) with a transfer coating technique only exerts a (comparatively) small pressure onto the porous layer (10) and thereby ensures a sufficient coating weight on the surface of the porous layer (sufficient to achieve desirable adhesive properties) without causing blockage of pores.

All embodiments, features and effects described above in connection with the medical dressing according to the first aspect of the invention are applicable, mutatis mutandis, for the above described method according to the second aspect of the invention.

In the claims, the terms "comprising" and "comprise(s)" do not exclude other elements or steps, and the indefinite article "a" or "an" does not exclude a plurality of elements or steps.

The mere fact that certain measures are recited in mutually different dependent claims does not indicate that a combination of these measured cannot be used to advantage.

BRIEF DESCRIPTION OF THE DRAWINGS

These and other aspects of the invention will now be shown in more detail, with reference to the appended drawings showing exemplary embodiments of the invention, wherein:

FIG. 3A shows a bottom view [first side (11)] of a dressing in accordance with the invention with a focus on the outermost second coating (2), comprising through openings (3) in said second coating, which "expose" the first coating (1) on the porous layer (10).

FIG. 3B shows a dressing and view similar to FIG. 3A with a "chess-board" coating pattern of through openings (3).

DETAILED DESCRIPTION OF EMBODIMENTS

In the following, the present invention in accordance with the first and second aspect as disclosed above is described in further details, and in reference to the Figures and the Examples.

Figure 1:
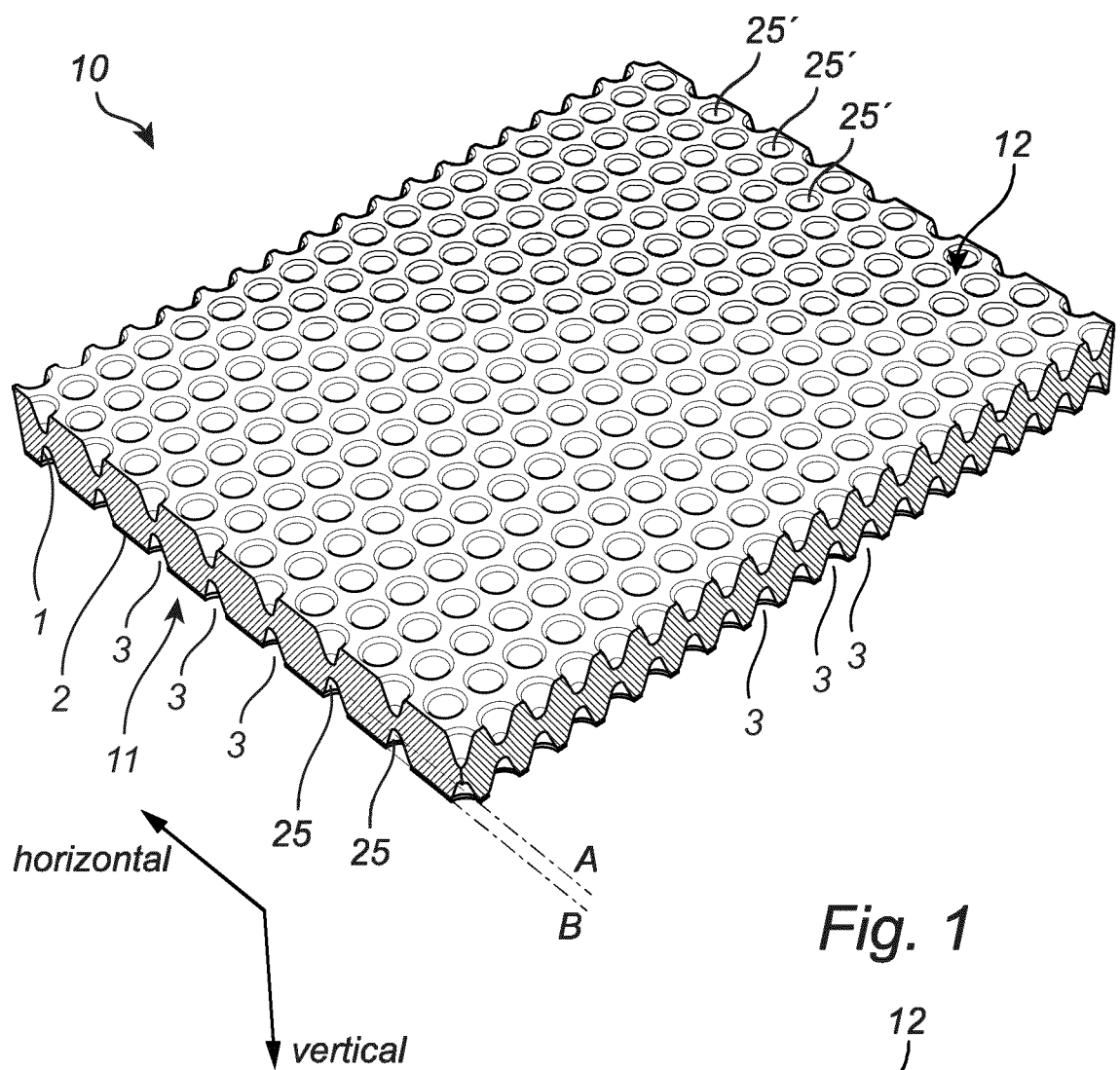
FIG. 1 shows a top perspective view of dressing in accordance with the invention (having depression points).
Figure 1A:
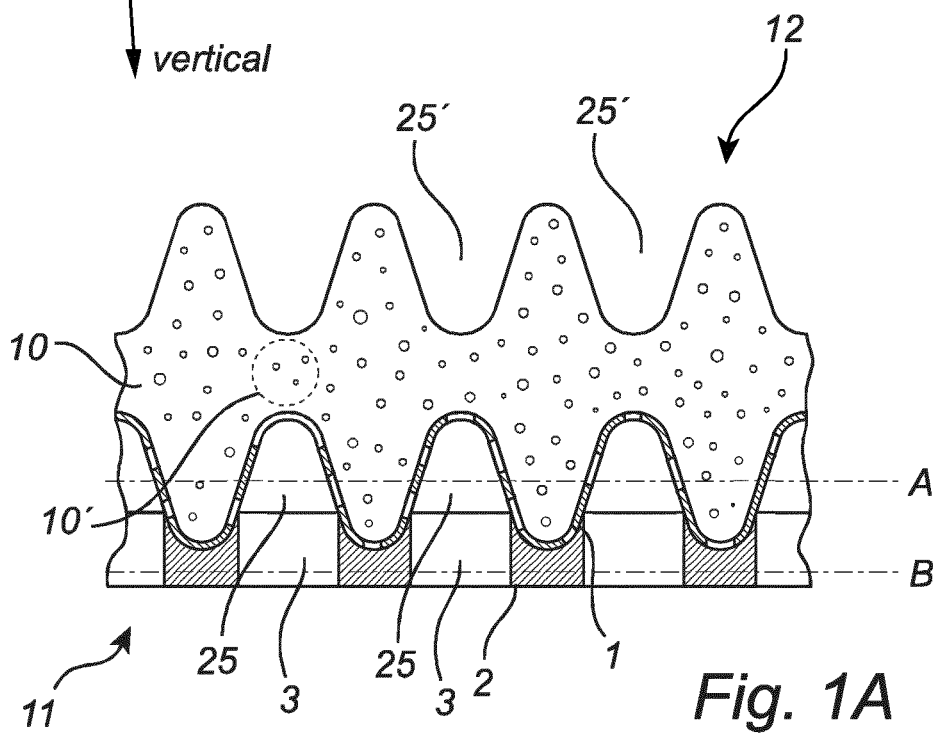
FIG. 1A shows a cross-sectional view of the dressing of FIG. 1, highlighting the pattern of depression points and the arrangement of the two coatings in two planes.

FIG. 1 shows a foam layer (10) in accordance with the present invention that is coated with a first coating (1) and a second coating (2), which are applied onto the first side (11) of the porous layer. This "doubly coated" porous layer is adapted to face an area of application in use, in particular adapted to face a wound area. The first coating is directly applied onto said first side (11) of the foam layer (10) and also at least partly coats the inside of the depression points (see cross-sectional view in FIG. 1A and SEM photograph of FIG. 1B). The second coating (2) (which is meant to function as an adhesive layer) is applied (directly in this specific embodiment) onto the first coating (1) and has a regular array of through openings (3) that (in this specific embodiment) substantially coincide with the pattern of depression points, such that at least a portion of the surface area within depression points is void of the second coating.

At least a portion of the surface area in the depression points is coated with said first coating which is preferably a hydrophobic coating. By coating parts of the porous foam layer, in particular those parts that are "exposed" to the wound since they align with the perforations (through openings as necessary for reasons of fluid transport from the wound into the foam) in the second coating, fluid transport through the adhesive layer and into further into the foam layer is facilitated while, at the same time, reflux of exudate from the foam layer back into the wound and/or in-growth of wound tissue through the openings of the second coating can be reduced due to the presence of coating (1) covering and "hydrophobicizing" (i.e. making (more) hydrophobic) those areas of the porous layer that would otherwise be directly "exposed" to the wound or skin surface.

The exemplary dressing of FIG. 1 comprises a regular pattern of depression points (25) and (25') in the two opposing sides (11) and (12), respectively, of the foam layer (10). The depression points in opposite sides are coaxial to each other and separated from each other by common "bottom" portions (10'), which represent foam portions that are more strongly depressed than adjacent foam segments that are not located underneath a depression point. This is perhaps best illustrated in FIG. 1b. These depression points may, for example, be "imprinted" onto the nascent foam as part of the manufacturing of the foam (i.e. in-line) or may be "imprinted" onto the as-made foam in a post-manufacturing step.

In embodiments of the present invention, the foam layer (10) has a pattern of ultrasonically made depressions present in the two opposing sides of the layer, the depressions in the opposing sides being coaxial to each other and separated from each other by a common bottom portion which is compressed to a higher extent than the remaining parts of said layer.

In such a layer, the compression of the layer will be larger in regions surrounding the depressions than in other regions of the layer, which means that the spreading and retention of fluid in such a layer can be varied by varying the pattern of depressions. Furthermore, the presence of regions between the depressions having a lower compression makes the body conformable to the patient by rendering the overall dressing more "bendable" due to the presence of these depression points.

In embodiments of the present invention, the porous layer is a foam having a plurality of foam cells and, in a region around each depression, the size of the foam cells increases (and the cell shape changes) in a direction from said common bottom portion to the respective opening of the depression, as well as in an outward direction from said common bottom portion parallel to the surfaces of said layer containing said depressions.

In embodiments of the present invention and in order to provide a desired conformability of such a layer, the common bottom portions of the depressions in the patterns of depression are not connected to each other, and distanced from each other by at least 10% of the thickness of said layer, optionally at least 20% of the thickness of said layer.

The patterns of depressions preferably is regular, both in regard to relative spacing and depth, but irregular patterns or different depths of the depressions are also within the scope of the present invention.

In embodiments of the present invention, the layer (foam) material in the bottom portions of the depression is at least partly fused together so that only a comparatively small amount of very small cells are present in the common bottom portions.

In the preferred embodiment, said porous layer (10) is made of a polyurethane foam but other foams of thermo-set or thermoplastic material can alternatively be used.

One method of making such a layer, in particular a foam layer that has a pattern of depressions in two opposite sides comprises a step of feeding said layer between a counter roller having a pattern of protrusions projecting from its outer surface and a horn of an ultrasound welding device, optionally applying one or more further layers (of absorbent material) on at least one side of said layer (10), and attaching said layers to said primary layer, and cutting individual wound pads from the layer of compressed thermoplastic or thermo-set material.

Figure 1B:
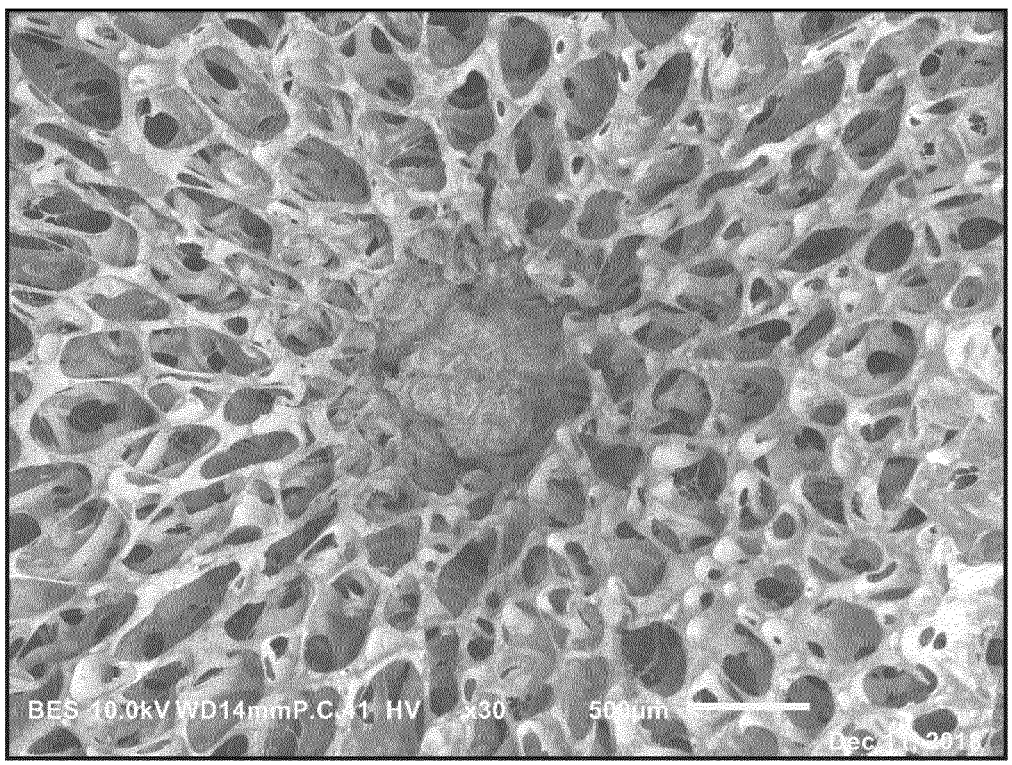
FIG. 1B shows an SEM photograph of an open cell foam that has been coated with 50 gsm of silicone gel in an impregnation coating step, applying pressure so that the silicone gel penetrates into the pores and also into a depression point. The silicone gel is discernible from the skeleton structure of the foam as thin white film.
Figure 1C:
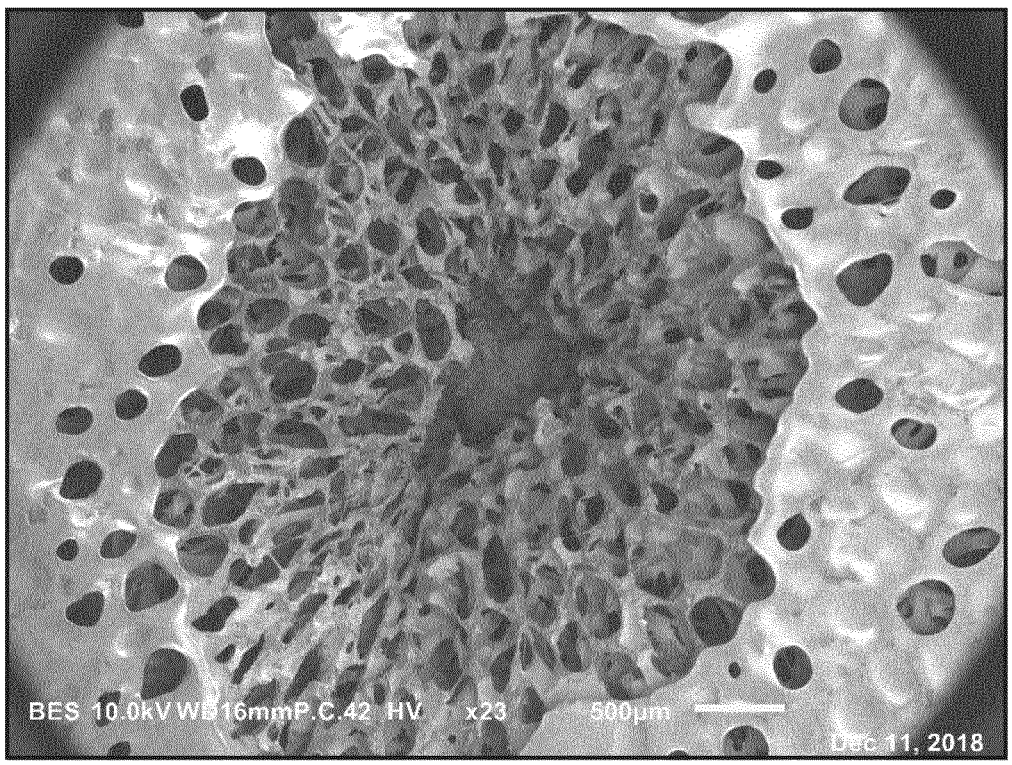
FIG. 1C shows an SEM photograph of the same open cell foam as shown in FIG. 1B, that now has been coated with 50 gsm of silicone gel in an impregnation coating step, and also with 100 gsm of silicone gel applied by transfer coating on top of foam already impregnated. The silicone gel as impregnated is discernible from the skeleton structure of the foam as thin white film while the adhesive silicon layer on top is discernible as a relatively thick film. The holes shown are not through openings in the meaning of the present invention but instances of the film breaking up as a consequence of the coating step.

Now turning back to the main aspect of the present invention: FIG. 1b also illustrates the principle of the present invention, according to which the first coating (1), which is preferably a hydrophobic coating, is "closer" to the foam layer (10), and hence farther away from the wound, than the "outer" second coating (2), which is generally applied onto said first coating (1) and which has the primary function of being an adhesive layer. As a consequence, plane (B), which represents the average position of the outer surface of the second coating, is farther away from the first side (11) of the foam (10) than plane (A), which represents the average position of the outer surface of the first coating.

No limitations exist in regard to the first (1) and the second (2) coating, other than that the first coating should be suitable to render the porous layer (more) hydrophobic and that the second coating should have adhesive properties.

In embodiments of the present invention, the first or the second coating comprise (optionally consist of) a silicone gel or the first and the second coating comprise (optionally consist of) a silicone gel.

In embodiments of the present invention, the silicone gel comprises a chemically cross-linked silicone gel (polydimethyl siloxane gel), for instance a platinum catalyzed 2-component addition hardening RTV-silicone. Examples of gels that can be used are SilGel 612 from Wacker-Chemie GmbH, Burghausen, Germany, and MED-6340 from NuSil Technology, Carpinteria, USA. Examples of adhesive gels useful in this context are also described in GB-A-2 192 142, GB-A-2 226 780 and EP-A1-0 300 620.

In embodiments of the present invention, the second coating may comprise or consist of hydrophobic polyurethane gels.

Figure 2:
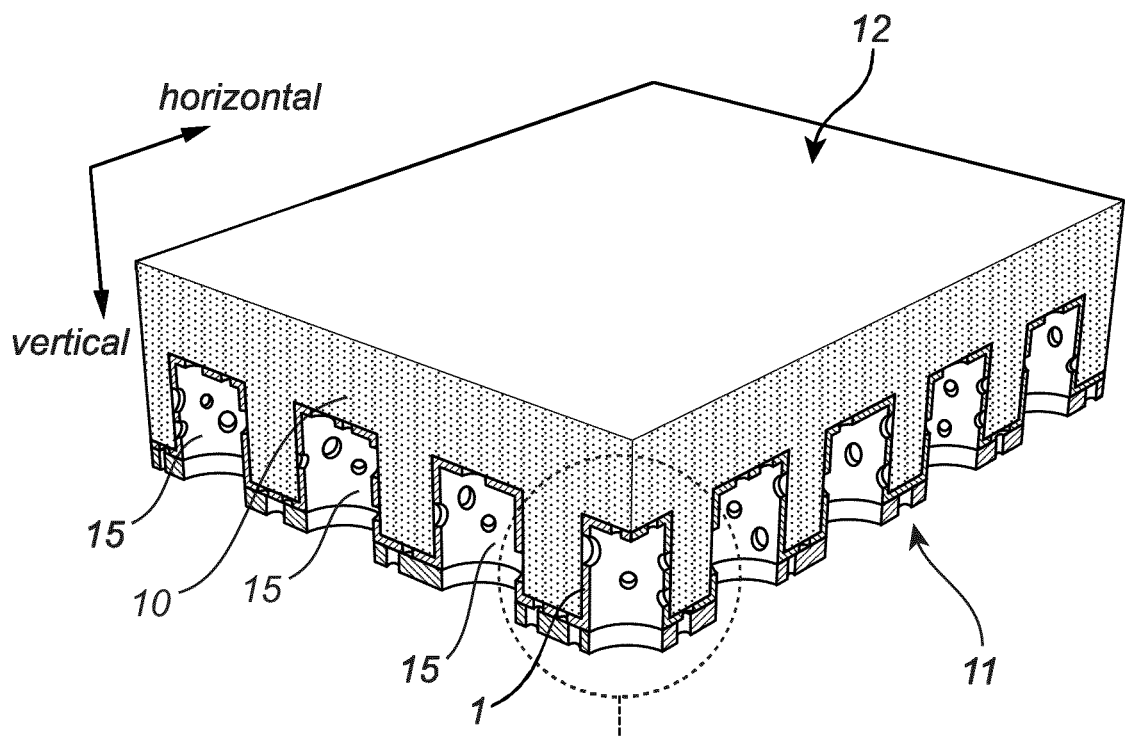
FIG. 2 shows a top perspective view of another dressing in accordance with the invention (having openings in the porous layer on the wound facing side).

FIG. 2 shows another embodiment of a medical dressing comprising a porous layer (10), here realized as a foam layer (10) having a first and second side, the first side being adapted to face an area of application in use, preferably adapted to face a wound area. In this embodiment, the foam layer (10) comprises a pattern of openings (15) on the first side (11) of the foam layer (10). The openings may be through-openings (i.e. fully penetrating through the thickness of the foam layer) or, as shown in FIG. 2, in a preferred embodiment, the openings (15) extend (only) into at least a portion of the foam layer (i.e. are not fully penetrating). The first side (11) of the foam layer (10) is coated with the coating (1) and then an adhesive layer [second coating (2)] having a pattern of through openings (3) that substantially coincide with the pattern of openings in the foam layer is coated over said first coating, such that at least a portion of the surface area within each opening in the foam layer is void of the adhesive layer.

Figure 2A:
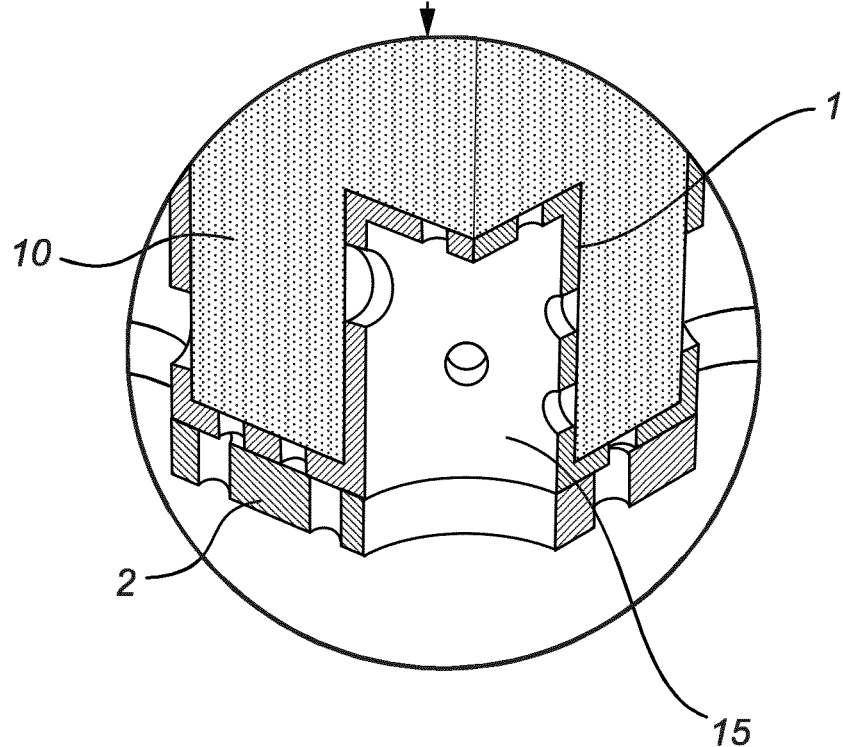
FIG. 2A shows a cross-sectional view of the dressing of FIG. 2, highlighting a not fully penetrating opening that is coated with the hydrophobic coating (1) on the inside and with the adhesive coating (2) on the outside, i.e. the surface of the porous layer (10). As explained in more detail in the description, neither coating (1) nor coating (2) are typically continuous, but both coatings are broken up. These "breaking points" in the coating must be distinguished from the through openings (3) as deliberately introduced into the second coating

As illustrated in FIG. 2A, at least a portion of the surface area in the openings (15) in the foam layer (10) is coated with a hydrophobic coating [first coating (1)], while the second coating (2) is primarily present on the outer surface of the first side (11) of the foam layer (10) and is coated on top of any first coating. Said first coating (1) is present in the area of the openings and may be present on the (entire other) outer surface of the first side of the foam layer. Also in this embodiment, fluid transport through the adhesive layer and into further into the foam layer is facilitated whilst, at the same time, minimizing reflux of wound exudate and/or in-growth of wound tissue. As will be shown in the Examples below, this effect minimizes any additional sticking of the dressing to the wound due to dried out refluxed wound exudate and therefore lowers the force required to remove the dressing after use, i.e. lowers or avoids additional wound trauma.

FIG. 3A and 3B show a bottom view [i.e. directed towards the first side (11)] of the foam layer (10) (not shown) of a medical dressing in accordance with the present invention. The foam layer is coated with a second coating (2), which comprises a pattern of through openings (3), which may be realized as circular openings (or a plurality of circular areas) as shown in FIG. 3A, or as shown in FIG. 3B, the second coating may be provided in a "chess-board" pattern. In either embodiment, the through openings (3) in the second coating (2) "expose" the first side (11) of the foam layer (10), which, however, is coated by the first coating (1).

Figure 4A:
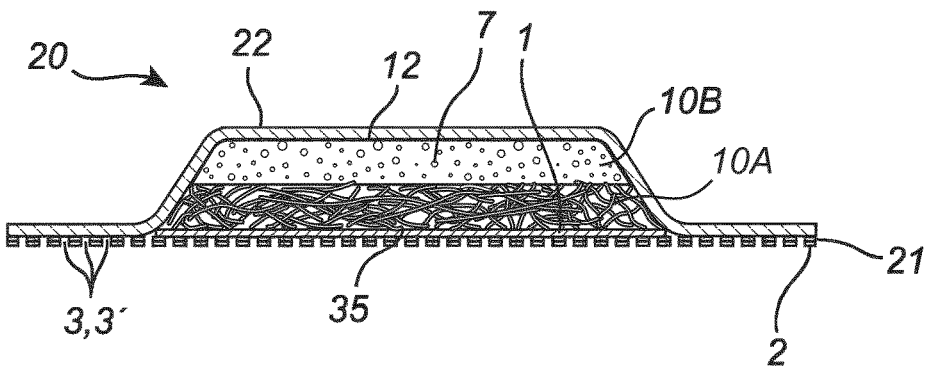
FIG. 4A shows a cross-sectional view of an island dressing that is in accordance with the present invention and that comprises a perforation layer (21) and a backing layer (22), as well as two adjacent but different porous layers 10A and 10B, realized as an array of network of fibers and as an open cell foam, respectively.

FIG. 4A/4B show exemplary embodiments of a medical dressing (20) according to the invention, the medical dressing comprising a composite porous layer (10A) and (10B) having a first and second side, the first side (11) being adapted to face an area of application in use, preferably adapted to face a wound area. In this embodiment porous layer (10A) is an array or network of fibers and porous layer (10B) is an open cell foam.

Figure 4B:
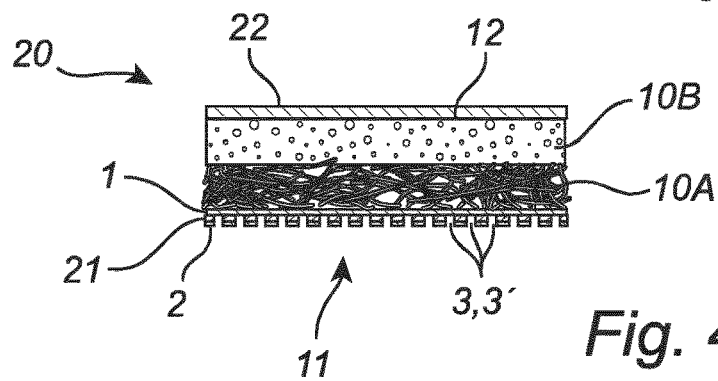
FIG. 4B shows a further detailed cross-sectional view of the island dressing of FIG. 4A.

As shown in FIG. 4A and FIG. 4B, the medical dressing preferably includes a perforated layer (21), which is arranged underneath the composite porous layer (10A)/(10B) but on the first coating (1). Said perforated layer (21) has a first side and a second side, wherein the second side is facing the first side of the composite porous layer, and wherein the second coating (2), i.e. the adhesive coating, is provided on the non-perforated portions of the first side of the perforated layer (21). The first coating (1) is provided on the first surface of the composite foam layer in at least those areas coinciding with the plurality of openings (3') in the perforated layer [which in turn coincide with the through openings (3) of the adhesive second coating (2)]. The perforated layer (21) includes a plurality of through openings (or through holes) of any suitable size and shape. The shape and size of the openings may be adapted to achieve a desirable degree of liquid transport from the wound to the foam layer. The perforated layer (21) may, for example, be made of a polyurethane film.

Figure 4C:
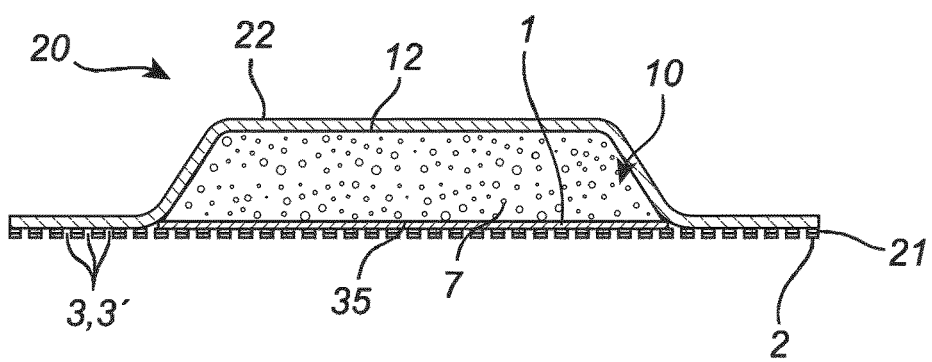
FIG. 4C shows a cross-sectional view of another island dressing that is in accordance with the present invention and that comprises one porous layer (10) realized as an open cell foam.

FIG. 4C shows a cross-sectional view of another island dressing that is in accordance with the present invention and that comprises one porous layer (10) realized as an open cell foam.

Figure 4D:
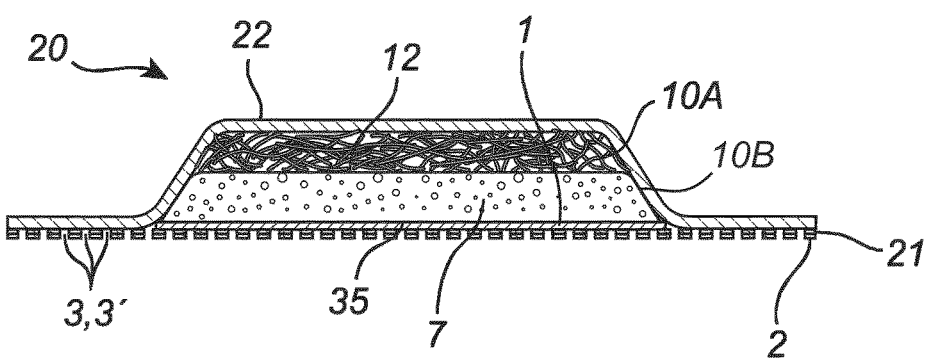
FIG. 4D shows a cross-sectional view of yet another island dressing that is in accordance with the present invention and that comprises a perforation layer (21) and a backing layer (22), as well as two adjacent but different porous layers 10A and 10B, realized as an array of network of fibers and as an open cell foam, respectively.

FIG. 4D shows a cross-sectional view of yet another island dressing that is in accordance with the present invention and that comprises a perforation layer (21) and a backing layer (22), as well as two adjacent but different porous layers 10A and 10B, realized as an array of network of fibers and as an open cell foam, respectively, which is similar to the embodiment of FIG. 4A but now has the foam layer closer to the wound.

Figure 5:
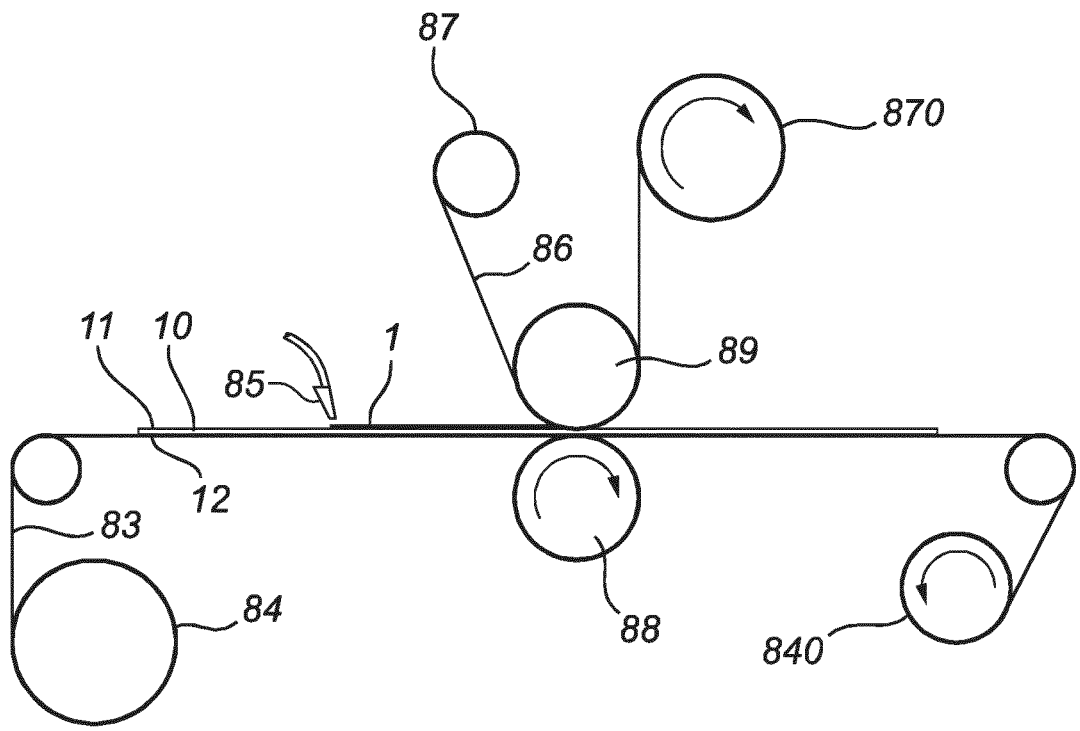
FIG. 5 shows an exemplary outline of a production line impregnating a porous layer with a first coating (1) of a silicone gel.

FIG. 5 illustrates an example for a method of fully or partially impregnating a porous layer (10) with a first coating (1) of a silicone gel. A web (82) of the porous layer (here realized as an open-cell foam) is transported on a paper web (83) fed from a roll of paper (84). The silicone gel leading to the first coating is applied via nozzle (85) is in its uncured state on the first side (11) of the open-cell foam layer (10). The layer (10) with the applied silicone gel is fed between two webs of process paper, the paper web (83) and a further paper web (86) from the paper roll (87), through a pair of press rolls (88) and (89). The foam layer with the applied silicone gel is squeezed between the press rolls for distributing the gel over the total cross section of the foam. After use, the paper web (86) is rolled up on the roll (870) and the paper web (83) is rolled up on the roll (840). Excessive silicone gel, if present, may be removed from the coated/impregnated foam layer (10), via these paper webs. With this process a layer (foam) that is partially or fully impregnated with silicone gel is achieved, wherein the gel is homogenously distributed through all or parts of the foam.

The foam web is thereafter heated for curing of the silicone gel. The curing of the silicone may be performed in a host blast furnace at a temperature of about 100° C. during about 1 to 5 minutes, preferably about 3 minutes.

The pressure between the press rolls may exemplarily be about 5 bar and said pressure is adjustable for controlled impregnation.

An exemplary velocity of the webs through the press rolls is about 2 to 5 m/min, preferably about 3 m/min.

Figure 6:
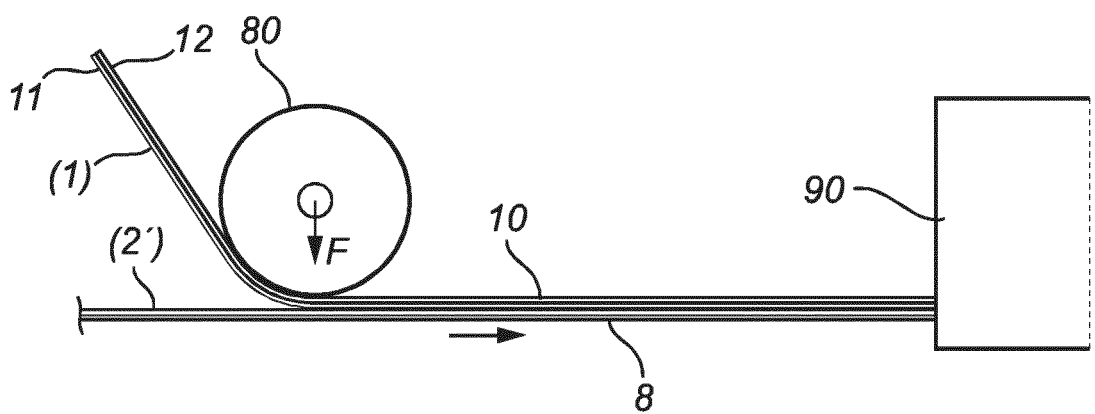
FIG. 6 shows an exemplary outline of a production line for transfer coating a second coating (2) onto said first coating (1).

FIG. 6 illustrates an exemplary method for applying a second coating (2) of silicone gel onto a porous layer (10) that is already coated with a first coating (1) of a silicone gel.

An exemplary apparatus includes a conveyer (not shown) on which a thin plastic film (8) is conveyed from left to right in FIG. 6. A layer of uncured gel mixture (2') is placed on the film (8). By gel mixture is meant a mixture of those components which form a gel after curing, including polymers that can react with one another to form a cross-linked structure. The porous layer (10) of absorbent foam material, already coated with the first coating (1) is applied to the layer (2') of uncured gel mixture with the aid of a roller (80), and the layers (2') as applied on coating (1) of layer (10) are then transported into an oven (90). The gel mixture of the second, or, in another embodiment of the first and the second coating, is/are cured in its passage through the oven (90) thus forming a cured gel coating (2) on the underside (11) of the foam material (10) as coated with a first (already or then) cured coating (1).

In embodiments of the present invention, the porous layer (10) is or comprises an array of fibers, in particular an array of superabsorbent fibers, or of gelling fibers (e.g. Exufiber®).

In accordance with the present invention, an array of fibers is any arrangement of fibers that has a larger extension in a (x-y) plane than in the direction perpendicular thereto (z-direction). Preferably the array of fibers has an area weight ("grammage") of 20-500 g/m$^2$, preferably 50-350 g/m$^2$.

In embodiments of the present invention, the porous layer (10) is or comprises a network of fibers, in particular a non-woven (e.g. Fibrella®), including hydroentangled fibers, in particular as present in non-woven network, or is or comprises an air-laid material comprising synthetic stable fibers and/or bi-component stable fibers and/or natural stable fibers and/or superabsorbent fibers and/or superabsorbent particles.

In accordance with the present invention, and also in accordance with the universally accepted understanding of the skilled person, a "non-woven" is defined as sheet or web structures bonded together by entangling fiber or filaments mechanically, thermally, or chemically, but not (as is conventionally done for fabrics) by weaving or knitting. Nonwovens are defined by ISO standard 9092 and CEN EN 29092. Non-woven substrates or webs are typically flat, porous sheets that are made directly from separate fibers or from molten plastic or plastic films.

In embodiments of the present invention, the porous layer (10) is or comprises a hydrophilic foam. In embodiments of the present invention, the porous layer (10) is or comprises a hydrophilic polyurethane foam.

In embodiments of the present invention, the porous layer (10) is characterized by a free swell absorptive capacity, corresponding to the maximum absorptive capacity, of at least 500 kg/m3, preferably at least 600 kg/m3, more preferably 700 kg/m3, as measured by EN 13726-1:2002. In embodiments of the present invention, the porous layer is characterized by a free swell absorptive capacity, corresponding to the maximum absorptive capacity, of from 800 to 2500 kg/m3 as measured by EN 13726-1:2002.

In embodiments of the present invention, the hydrophilic foam material is an open-cell porous hydrophilic foam having a density of 60 to 180 kg/m3, preferably 80 to 130 kg/m3, more preferably 90 to 120 kg/m3, as measured according to standard method ISO 845:2006.

As used herein, the term "open-cell" refers to the pore (or cell) structure of the foam, wherein the pores in a pore structure are connected to each other and form an interconnected network with pathways for fluid flow through the foam material. "Substantially" open-cell structures have at least 95%, preferably at least 99% of pores that are connected with at least one other pore.

In embodiments of the present invention, the porous layer (1) is or comprises a hydrophilic polyurethane foam that is obtained from a prepolymer comprising or being an isocyanate-capped polyol or isocyanate-capped polyurethane. These hydrophilic foams have proven to be particularly useful in wound dressings as they have improved absorption capacity vis-à-vis other foam materials known from the art. Furthermore, these foams can be coated with the first coating (1) and the presence of said first coating, together with the absorptive capacities of the foam, minimize or essentially avoid reflux of wound exudate, once it has been absorbed in this foam, back to the wound or the skin of a patient.

In accordance with the present invention, the term "prepolymer" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to a polymer or oligomer the molecules of which are capable of entering, through reactive groups, into further polymerization and thereby contributing more than one structural unit to at least one type of chain of the final polymer.

In embodiments of the present invention, the prepolymer derives from a reaction between a polyol and a diisocyanate compound selected from the group consisting of hexamethylene diisocyanate (HDI), toluene diisocyanate (TDI), methylene diphenyl diisocyanate (MDI), or isophorone diisocyanate (IPDI), or any mixture thereof.

In embodiments of the present invention, the polyol is selected from the group consisting of polyester polyols, polyacrylate polyols, polyurethane polyols, polycarbonate polyols, polyether polyols, polyesterpolyacrylate polyols, polyurethane polyacrylate polyols, polyurethane polyester polyols, polyurethane polyether polyols, polyurethane polycarbonate polyols and polyester polycarbonate polyols, among others, in particular polycondensates of di or optionally tri-, and tetraols as well as di or optionally tri- and tetracarboxylic acids or hydroxycarboxylic acids or lactones.

Exemplary suitable diols are ethylene glycol, butylene glycol, diethylene glycol, triethylene glycol, polyalkylene glycols such as polyethylene glycol, and also 1,2-propanediol, 1,3-propanediol, 1,3-butanediol, 1,4-butanediol, 1,6-hexanediol and isomers, neopentyl glycol or neopentyl glycol hydroxypivalate. In addition, polyols such as trimethylolpropane, glycerol, erythritol, pentaerythritol, trimethylolbenzene or trishydroxyethyl isocyanurate are also within the scope of the present invention.

In embodiments of the present invention, the prepolymer derives from a reaction between a polyol and a diisocyanate compound that is aliphatic. For example, in embodiments of the present invention, the diisocyanate compound is or comprises hexamethylene diisocyanate (HDI). Accordingly, in embodiments of the present invention, the prepolymer is or comprises an hexamethylene isocyanate-capped polyol or hexamethylene isocyanate-capped polyurethane.

In embodiments of the present invention, the prepolymer is or comprises a hexamethylene isocyanate-capped polyethylene glycol.

In embodiments of the present invention, the prepolymer derives from a reaction between said polyol and a diisocyanate compound that is aromatic. For example, in embodiments of the present invention, the diisocyanate compound is or comprises toluene diisocyanate (TDI), methylene diphenyl diisocyanate (MDI). Accordingly, in embodiments of the present invention, the prepolymer is or comprises a toluene isocyanate-capped polyol or a methylene diphenyl isocyanate-capped polyol or toluene isocyanate-capped polyurethane or methylene diphenyl isocyanate-capped polyurethane.

In embodiments of the present invention, the prepolymer is or comprises a toluene isocyanate-capped polyethylene glycol. In embodiments of the present invention, the prepolymer is or comprises a methylene diphenyl isocyanate-capped polyethylene glycol.

In embodiments of the present invention, the porous layer (10) comprise(s) at least one antimicrobial agent.

In embodiments of the present invention, the antimicrobial agent comprises silver. In embodiments of the present invention, the silver is metallic silver. In embodiments of the present invention, the silver is a silver salt.

In embodiments of the present invention, the silver salt is silver sulfate, silver chloride, silver nitrate, silver sulfadiazine, silver carbonate, silver phosphate, silver lactate, silver bromide, silver acetate, silver citrate, silver carboxymethyl cellulose (CMC), silver oxide. In embodiments of the present invention, the silver salt is silver sulfate.

In embodiments of the present invention, the antimicrobial agent comprises a monoguanide or biguanide. In embodiments of the present invention, the monoguanide or biguanide is chlorhexidine digluconate, chlorhexidine diacetate, chlorhexidine dihydrochloride, polyhexamethylene biguanide (PHMB) or a salt thereof, or polyhexamethylene monoguanide (PHMG) or a salt thereof. In embodiments of the present invention, the biguanide is PHMB or a salt thereof.

The person skilled in the art realizes that the present invention by no means is limited to the exemplary embodiments described herein. For example, the medical dressing according to invention may comprise additional structural layer(s) in fluid communication with the porous layer to further optimize desirable properties and/or to achieve additional functionalities The invention is further illustrated in the following Examples. Unless otherwise specified, all experiments and tests described herein were performed at standard laboratory conditions, in particular at room temperature (20° C.) and standard pressure (1 atm.). Unless indicated otherwise, all indications regarding percentages are meant to refer to percentage by weight.

The present invention also may be defined in accordance with the following numbered embodiments, either alone or in combination with the other embodiments as described herein:

1. A medical dressing (20) comprising
   a porous layer (10) having a first side (11) and a second side (12), wherein said first side and said second side are opposite to each other and extend in the horizontal direction of said porous layer;
   a first coating (1) extending along at least a portion of the surface area of said first side (11) of said porous layer (10), optionally along essentially the entire surface area of said first side (11), wherein said first coating (1) has a first surface facing away from said first side of said porous layer;
   a second coating (2) extending along said first side (11) of said porous layer (10), said second coating (2) comprising a pattern of through openings (3), wherein said second coating (2) has a first surface facing away from said first side (11) of said porous layer (10);
   wherein said first coating (1) extends along at least those portions of the surface area of said first side (11) of said porous layer (10) that coincide with the through openings (3) of said second coating (2); and
   wherein said first surface of said second coating (2) extends in a plane (B) that is farther away, in the vertical direction, from the first side (11) of said porous layer (10), than the corresponding plane (A) defined by the first surface of said first coating (1).
2. The medical dressing according to embodiment 1, wherein said porous layer is an absorbent layer, optionally, wherein said absorbent layer comprises or is a foam material, an array of fibers or a network of fibers, or any combination thereof.
3. The medical dressing according to embodiment 1 or embodiment 2, wherein the second coating (2) has a primary function of being adhesive while the first coating (1) has a primary function of rendering the first side of the porous layer (10) hydrophobic or more hydrophobic.
4. Medical dressing according to any of the preceding embodiments, wherein said pattern of through openings (3) in said second coating (2) is a regular geometric pattern or array, preferably represents a circular, rectangular or trapezoidal array of through openings (3).
5. The medical dressing according to any of the preceding embodiments, wherein said second coating (2) is an adhesive coating, optionally a silicone based adhesive coating.
6. The medical dressing according to any of the preceding embodiments, wherein said first coating (1) is a hydrophobic coating, optionally, wherein said coating is a silicone gel coating.
7. The medical dressing according to any one of the preceding embodiments, wherein said second coating (2) has a coating weight of from 50 g/m² to 500 g/m², optionally from 80 g/m² to 300 g/m².
8. The medical dressing according to any one of the preceding embodiments, wherein said porous layer (10) is or comprises a hydrophilic open-cell foam, or is or comprises an array of gelling fibers, hydro-entangled fibers, and/or superabsorbent fibers, or is or comprises a woven or a non-woven network of fibers.
9. The medical dressing according to any of the preceding embodiments, wherein the thickness of said porous layer (10) is from 0.5 mm to 30 mm, optionally from 1 mm to 15 mm, optionally thereto from 1 mm to 10 mm.
10. The medical dressing according to any of the preceding embodiments, wherein the first coating (1) has penetrated into at least 10% of the thickness of the porous layer (10), optionally wherein the first coating (1) has penetrated into at least 40% of the thickness of the porous layer (10) optionally thereto wherein the first coating (1) has penetrated into essentially the entire thickness of the porous layer (10).
11. The medical dressing according to any one of the preceding embodiments, wherein said medical dressing (20) comprises a further porous layer, wherein said further porous layer is an absorbent layer, optionally, wherein said further porous layer comprises or is a foam material, an array of fibers or a network of fibers, or any combination thereof.
12. The medical dressing according to any one of the preceding embodiments, wherein said porous layer (10) comprises a pattern, optionally a regular pattern, of depressions (25), wherein said pattern of depressions (25) is present on both said first side and said second side of said porous layer, wherein said pattern of depressions (25) on the first side is coaxial to the pattern of depressions (25') on the second side, and wherein the two patterns of depression (25, 25') are separated from each other by a common portion (10') of the porous layer, which portion (10') is compressed to a larger extent than the remaining parts of said porous layer (10).
13. The medical dressing according to embodiment 12, wherein said pattern of depressions (25, 25') is the result of ultrasonic treatment.
14. The medical dressing according to any one of embodiments 1 to 11, wherein said porous layer comprises a pattern, optionally a regular pattern, of openings (15), wherein said pattern of openings (15) is provided in said first side (11) of said porous layer (10), optionally wherein said openings (15) do not fully penetrate said porous layer (10).
15. The medical dressing according to embodiment 14, wherein said pattern of openings (15) is the result of laser treatment or treatment by heated pins.
16. The medical dressing according to any one of embodiments 12 to 15, wherein said pattern of openings (15) or depressions (25) in the porous layer (10) substantially coincides with said pattern of through openings (3) in said second coating (2).
17. The medical dressing according to any one of the preceding embodiments, wherein said medical dressing (20) further comprises a perforation layer (21) comprising a pattern of through openings (3'), wherein said perforation layer (21) has a first side and a second side wherein said first side of said perforation layer is arranged to face away from the first side (11) of the porous layer (10), wherein said second coating (2) is provided on said first side of said perforation layer (21), and wherein said pattern of through openings (3) in said second coating (2) substantially coincides with said pattern of through openings (3') in said perforation layer (21).

18. The medical dressing according to any one of embodiments 1 to 16, wherein said first coating (1) is provided in direct physical contact with the surface area of said first side (11) of the porous layer (10), and wherein said second coating (2) is provided in direct physical contact with said first coating (1)
19. The medical dressing according to any one of the preceding embodiments, wherein said medical dressing (20) further comprises a backing layer (22) extending along the second side (12) of the porous layer (10).
20. A method for manufacturing a medical dressing, said method comprising the steps of:
   providing a porous layer (10) having pores or openings;
   applying a first coating (1) onto a first side (11) of said porous layer,
   compressing said porous layer (10) such that said applied first coating (1) at least partly penetrates into said pores or openings of the porous layer,
   directly or indirectly applying a second coating (2) over said first side (11) of said porous layer (10),
   introducing a pattern of through openings (3) into said second coating (2), either prior to said step of applying a second coating (2) or during said step of applying a second coating (2) or after said step of applying a second coating (2);
   wherein, after conclusion of these steps, said first coating (1) extends along at least those portions of the surface area of said first side (11) of said porous layer (10) that coincide with the through openings (3) as introduced into said second coating (2).
21. The method according to embodiment 20, wherein the weight of said second coating (2) as applied is at least 30% more, optionally at least 50% more than the weight of the first coating (1) as applied.
22. The method according to embodiment 20 or embodiment 21, wherein said first coating (1) is or comprises a first silicone composition which is applied on said first side of said porous layer in a substantially uncured state, and wherein said method further comprises a step of curing said first silicone composition after said step of compressing said porous layer.
23. The method according to embodiment 22, wherein said second coating (2) is or comprises a second silicone composition which is the same as or different from the first silicone composition and which is applied over said first side (11) of said porous layer in a substantially uncured state, and wherein said method further comprises a step of curing said second silicone composition after it has been applied over said first coating (1).
24. The method according to embodiment 23, wherein said second coating (2) is or comprises a second silicone composition which is the same as or different from the first silicone composition and which is applied over said first side (11) of said porous layer in a substantially uncured state, wherein said method further comprises a step of curing said second silicone composition, and wherein said step of curing said first silicone composition and said step of curing said second silicone composition is performed at the same time.
25. The method according to any one of embodiments 20 to 24, wherein said porous layer (10) comprises a pattern of depressions or pattern of openings.
26. The method according to any one of embodiments 20 to 25, wherein the first coating is applied by a method comprising a penetration step and the second coating is applied by method comprising a transfer coating step, wherein said a pattern of through openings is introduced during said transfer coating step.

The invention is illustrated in the following by non-limiting Examples:

EXAMPLES

Preparation of a Compressed Porous Layer with First and Second Silicone Gel Coating Samples of a porous layer (10) have been manufactured by feeding of an uncompressed open-celled polyurethane foam product i.e. Lyofoam Max 15 cm×15 cm, Mölnlycke Health Care, ref No 603204, having a thickness of 5 mm through the gap between the horn of the ultrasonic welding device DPC (20 kHz) from Dukane and a counter roller having rows of cylindrical protrusions extending around the peripheral surface thereof in a regular pattern. The height of each protrusion was 3 mm and the diameter was 1.4 mm. The distance between adjacent protrusions was 5 mm and between the rows was 4.3 mm. After passage of the ultrasonic welding device 5, the thickness of the compressed foam layer was 4 mm.

The first layer of silicone gel coating is made by directly applying 40 gsm of SilGel 612 from Wacker onto a polyethylene coated paper (120 g/m$^2$) from Mondi Silicart. The compressed Lyofoam Max product is applied onto the uncured silicone layer. The laminate is then exposed to a press roll as shown schematically in FIG. 5 with a pressure of approximately 3 Bar. The porous layer as impregnated by the first coating is then removed from the paper.

A second layer of silicone gel coating is created by directly applying 125 gsm of SilGel 612 onto a polyethylene coated paper (120 g/m$^2$) from Mondi Silicart. The precoated layer is then applied onto the porous layer as coated with the first coating, and a low pressure of approximately 4 mBar is applied to keep the precoated product flat during curing of the silicone gel at a temperature of 90 degree Celsius for 5 minutes. The process paper is removed before testing of the product.

Measuring Reduced "Reflux" for "Double Coated" Porous Layer Vs Single Coated Porous Layer The clinical situation of interest is the following: in a porous layer according to the art, which is only "singly" coated by a silicone gel coating that has perforations, exudate initially transported away from the wound is not fully retained by the porous layer but at least partly "trickles" back to the wound area ("reflux") and eventually dries out in the area between wound dressing and wound. Wound exudate typically contains electrolytes, nutrients, proteins, protein digesting enzymes (eg matrix metalloproteinases (MMPs)), growth factors as well as various types of cells, all or some of which have the effect to (further) adhere the dressing to the wound, above and beyond the adhesion already provided by the adhesive coating of the wound dressing. However, too high a peak adhesion upon drying is undesirable as it will cause pain in a clinical situation.

Figure 7:
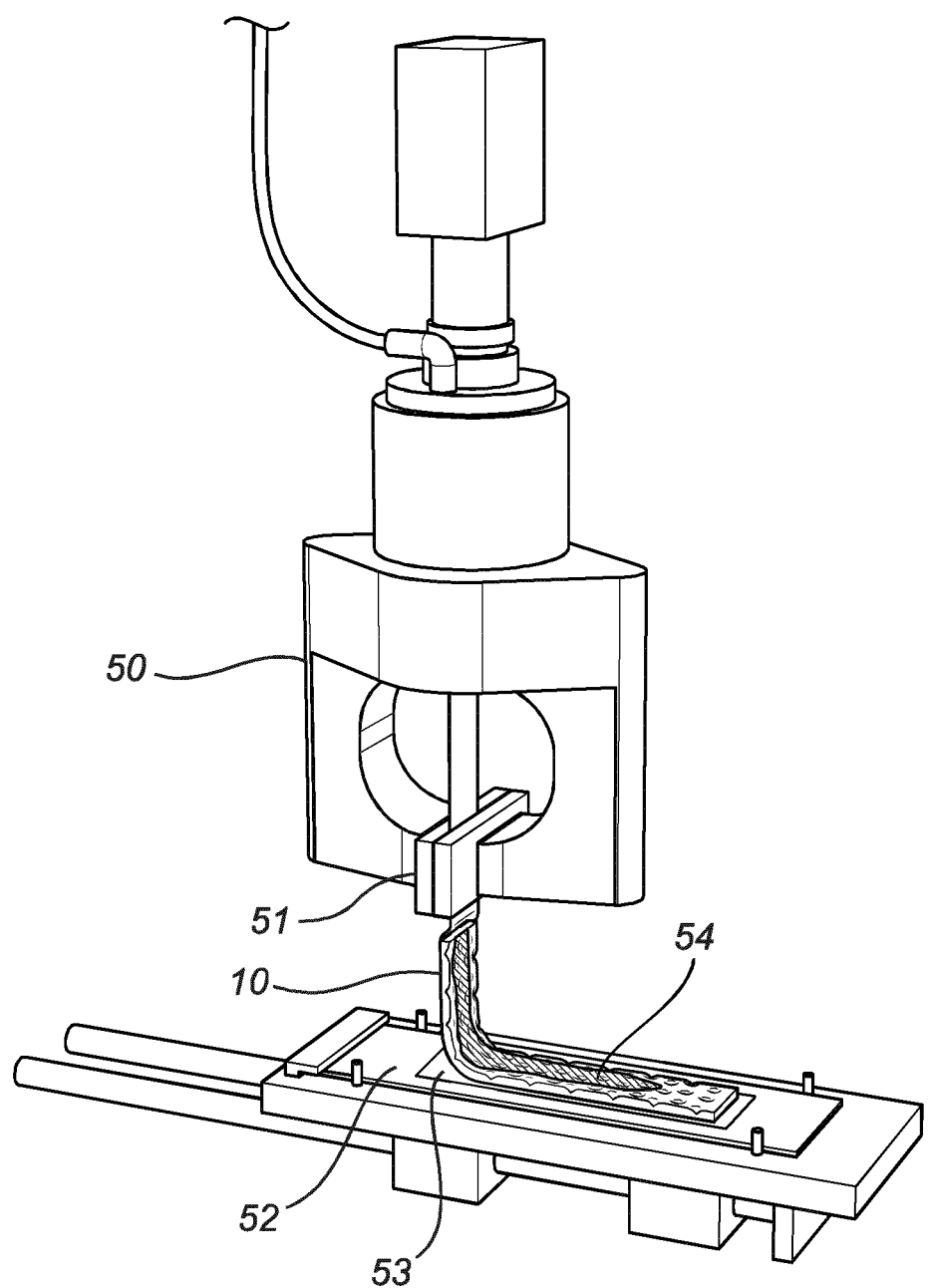
FIG. 7 shows a schematic drawing of the test apparatus used to measure the effect of the coating in accordance with the present invention has on the force that is required to remove a wound dressing from a wound surface.

The following test was developed to mimic this clinical situation and to provide a performance parameter that can be measured: Reference is made to FIG. 7 showing the tensile test head (50) that is used to determine the force required, i.e. peak adhesion to remove the "dressing" from the "skin":

1. Cut or punch test pieces of the porous layer (10) (as described above) into strips of 25±1 mm times at least 100 mm, preferably 120 mm in MD.
2. Acclimate the test pieces in 23±2° C. and 50±5% controlled humidity for 24 h.

3. Place double adhesive tape on a steel plate (52) (5×20 cm). Place colour printing paper (100 gsm) (3×8 cm) on the double adhesive tape, covering the start mark with about 0.5 cm. Calendar the paper in order to make it adhere well to the plate, without trapping air underneath. The resulting "paper on tape" (53) is meant to mimic human skin.
4. Wet the test pieces (10) with 3 ml horse serum using a pipette, covering a 20 mm wide and 70 mm long field. Make sure that the horse serum is not distributed over the entire width of the test piece (see shaded area of (10) in FIG. 7).
5. Place the test piece (10) over the "paper on tape" strip (53).
6. Punch out a 25×100 mm piece of an Avance foam, Mölnlycke Health Care ref no 62551 (part of Avance foam kit ref 662252), and place it over each of the test pieces.
7. Place 4 steel plates with test pieces and Avance foam next to each other.
8. Place two steel plates (5×20 cm) on top of the Avance foam.
9. Place weights on the steel plates. The total weight including steel plates is 5420 g.
10. Place the entire assembly of wound surface as mimicked by the paper and wound dressing under pressure in an oven set to 37° C.
11. After 24 h take assembly out of the oven.
12. Remove the weights, steel plates and Avance foam.
13. Place the steel plate (52) with the test piece (10) in the slide and clamp one end of the test piece in the tensile tester clamp (51). Testing done at 90° angle (see FIG. 7).
14. Settings for tensile tester: Speed 100 mm/min, gauge distance 50 mm, mean load calculation between 10-60 mm.
15. Start the test and delaminate the specimen from the steel plate and measure peak force required to do so.

Figure 8:
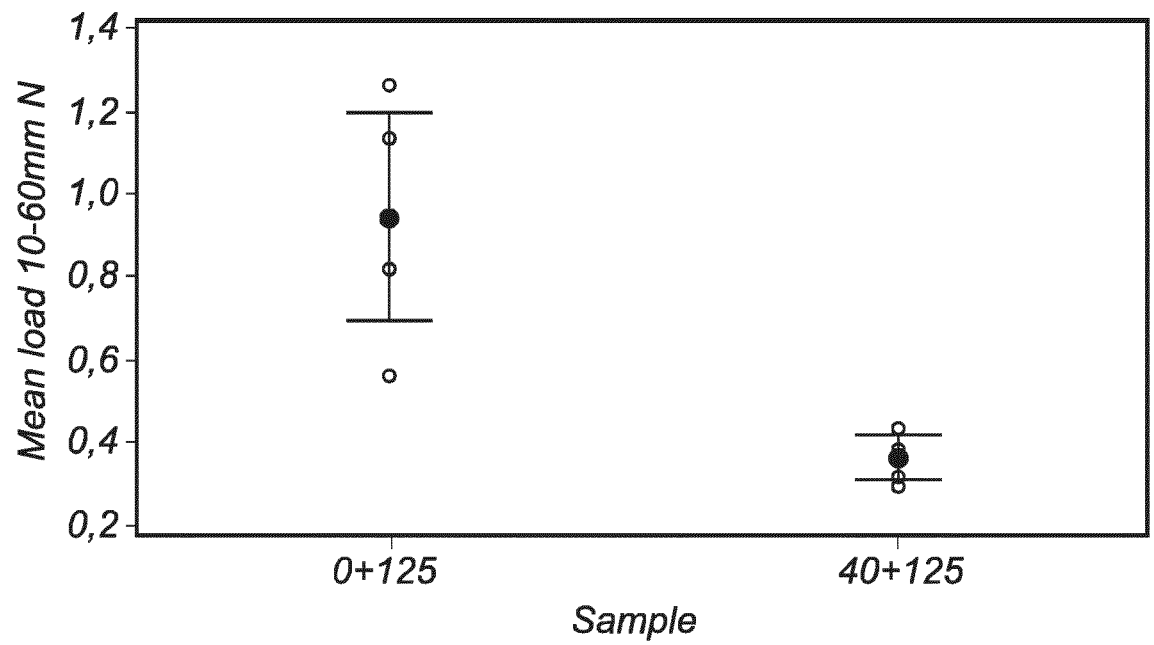
FIG. 8 shows the results of a test conducted with the apparatus of FIG. 7.
Figure 9:
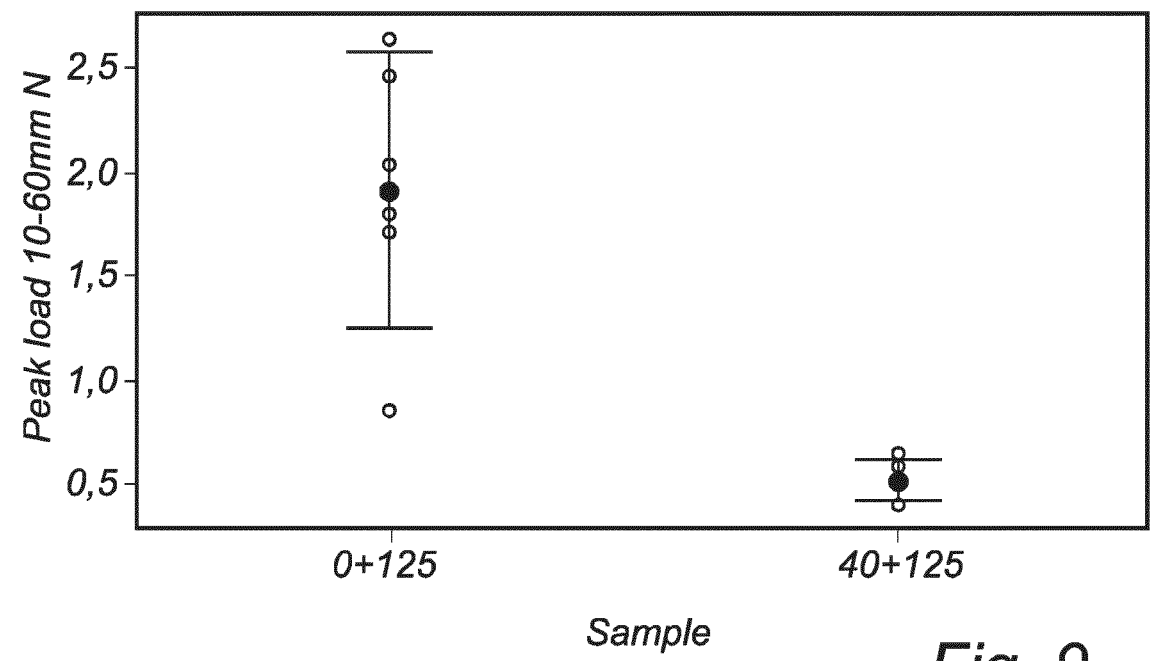
FIG. 9 shows an alternative representation results of the test conducted with the apparatus of FIG. 7.

The results of the test conducted on a "single coated" porous layer as know from the art (comparative example) and "doubly coated" porous layer in accordance with the present invention are shown in FIGS. 8 and 9. FIG. 8 shows the mean load as measured in accordance with the test described above. The sample on the left is a porous layer as coated only with the adhesive coating (2), (125 gsm), which has through openings (3), while the sample shown to the right is in accordance with an embodiment of the present invention and has a first coating (1) of 40 gsm covering all through openings as defined by the second coating (125 gsm). It can be seen that an undesirably high mean load is required to remove the porous layer form the "skin". FIG. 9 show the peak load required in an otherwise same setting. Again, more than four times the peak load is required to remove the sample as known from the art vis-à-vis the sample in accordance with the present invention.

Without wishing to be bound by theory, it is believed that the higher peak adhesion observed in single coating system is due to reflux in the uncoated areas as exudate dries out and the dressing gets "stuck" to the surface in these uncoated areas thus giving a measured increased "peak" for each such area.

The invention claimed is:

1. A medical dressing comprising
   a porous layer having a first side and a second side, wherein said first side and said second side are opposite to each other and extend in the horizontal direction of said porous layer;
   a first coating extending along at least a portion of the surface area of said first side of said porous layer, wherein said first coating has a first surface facing away from said first side of said porous layer;
   a second coating extending along said first side of said porous layer, said second coating comprising a pattern of through openings, wherein said second coating has a first surface facing away from said first side of said porous layer;
   wherein said first coating extends along at least those portions of the surface area of said first side of said porous layer that coincide with the through openings of said second coating; and
   wherein said first surface of said second coating extends in a plane (B) that is farther away, in the vertical direction, from the first side of said porous layer, than a corresponding plane (A) defined by the first surface of said first coating; wherein said porous layer comprises a pattern of depressions, wherein said pattern of depressions is present on both said first side and said second side of said porous layer, wherein said pattern of depressions on the first side is coaxial to the pattern of depressions on the second side, and wherein the two patterns of depression are separated from each other by a common portion of the porous layer, which common portion is compressed to a larger extent than the remaining parts of said porous layer; and wherein said pattern of depressions in the porous layer substantially coincides with said pattern of through openings in said second coating.

2. The medical dressing according to claim 1, wherein said porous layer is an absorbent layer.

3. The medical dressing according to claim 1, wherein the second coating has a primary function of being adhesive while the first coating has a primary function of rendering the first side of the porous layer hydrophobic or more hydrophobic.

4. The medical dressing according to claim 1, wherein (I) said pattern of through openings in said second coating is a regular geometric pattern or array; or:
   wherein (II) said second coating is an adhesive coating; or:
   wherein (III) said first coating is a hydrophobic coating; or:
   wherein (IV) said second coating has a coating weight of from 50 g/m$^2$ to 500 g/m$^2$.

5. The medical dressing according to claim 1, wherein (I) said porous layer is or comprises a hydrophilic open-cell foam, or is or comprises an array of gelling fibers, hydroentangled fibers, and/or superabsorbent fibers, or is or comprises a woven or a non-woven network of fibers; or:
   wherein (II) the thickness of said porous layer is from 0.5 mm to 30 mm.

6. The medical dressing according to claim 1, wherein the first coating has penetrated into at least 10% of the thickness of the porous layer.

7. A method for manufacturing a medical dressing, said method comprising the steps of:
   providing a porous layer having pores or openings;
   applying a first coating onto a first side of said porous layer,
   compressing said porous layer such that said applied first coating at least partly penetrates into said pores or openings of the porous layer,
   directly or indirectly applying a second coating over said first side of said porous layer, introducing a pattern of through openings into said second coating, either prior to said step of applying a second coating or during said step of applying a second coating or after said step of applying a second coating;

wherein, after conclusion of these steps, said first coating extends along at least those portions of the surface area of said first side of said porous layer that coincide with the through openings as introduced into said second coating; and wherein said steps produce the medical dressing of claim 1.

8. The method according to claim 7, wherein the weight of said second coating as applied is at least 30% more than the weight of the first coating as applied.

9. The method according to claim 7 or, wherein (I) said first coating is or comprises a first silicone composition which is applied on said first side of said porous layer in a substantially uncured state, and wherein said method further comprises a step of curing said first silicone composition after said step of compressing said porous layer.

10. The method according to claim 7, wherein (I) said porous layer comprises a pattern of depressions or pattern of openings, or:

wherein (II) the first coating is applied by a method comprising a penetration step and the second coating is applied by method comprising a transfer coating step, wherein said pattern of through openings is introduced during said transfer coating step.

11. The medical dressing according to claim 1, wherein the first coating extends along essentially the entire surface area of said first side.

12. The medical dressing according to claim 1, wherein the first coating has penetrated into essentially the entire thickness of the porous layer.

13. The medical dressing according to claim 2, wherein said absorbent layer is a foam material, an array of fibers, or a network of fibers, or any combination thereof.

* * * * *